Figure 1:
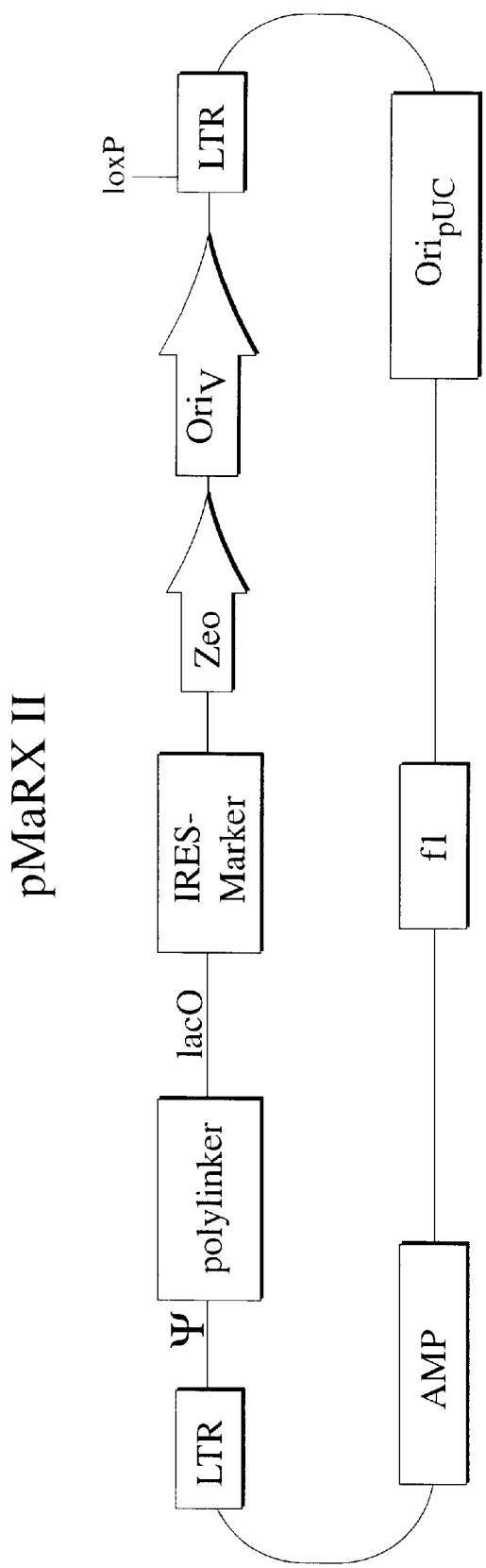

United States Patent [19]
Beach et al.

[11] Patent Number: 6,025,192
[45] Date of Patent: Feb. 15, 2000

[54] MODIFIED RETROVIRAL VECTORS

[75] Inventors: David Beach, Huntington Bay; Gregory J. Hannon, Huntington, both of N.Y.

[73] Assignee: Cold Spring Harbor Laboratory, Cold Spring Harbor, N.Y.

[21] Appl. No.: 08/716,926

[22] Filed: Sep. 20, 1996

[51] Int. Cl.[7] ............................ C12N 15/63; C12N 15/11; C07H 21/04

[52] U.S. Cl. ................... 435/320.1; 435/6; 435/172.1; 435/172.3; 536/23.1; 536/23.5; 536/24.1

[58] Field of Search .......................... 435/6, 69.1, 172.1, 435/172.3, 320.1; 536/23.1, 23.5, 24.1

[56] References Cited

U.S. PATENT DOCUMENTS

| | | | |
|---|---|---|---|
| 4,959,317 | 9/1990 | Sauer | 435/172.3 |
| 5,378,618 | 1/1995 | Sternberg et al. | 435/172.3 |

OTHER PUBLICATIONS

Blasina, A. et al., 1996, "Copy–Up Mutants of the Plasmid RK2 Replication Initiation Protein are Defective in Coupling RK2 Replication Origins", Proc. Natl. Acad. Sci USA 93:3559–3564.

Cheng, L. et al., 1996, "Use of Green Fluorescent Protein Variants to Monitor Gene Transfer and Expression in Mammalian Cells", Nature Biotechnol. 14:606–609.

Choulika, A. et al., 1996, "Transfer of Single Gene–Containing Long Terminal Repeats into the Genome of Mammalian Cells by a Retroviral Vector Carrying the cre Gene and the IoxP Site", J. Virol. 70:1792–1798.

Colas, P. et al., 1996, "Genetic Selection of Peptide Aptamers that Recognize and Inhibit Cyclin–Dependent Kinase 2", Nature 380:548–550.

Levy, J. et al., 1996, "Retroviral Transfer and Expression of a Humanized, Red–Shifted Green Fluorescent Protein Gene into Human Tumor Cells", Nature Biotechnol. 14:610–614.

Socolic, R. et al., 1996, "A Bicistronic Retrovirus Vector Containing a Picornavirus Internal Ribosome Entry Site Allows for Correction of X–Linked CGD by Selection for MDR1 Expression", Blood 87:42–50.

Suzuki, H. et al., 1996, "Infection of Human Cells by Murine Ecotropic Viruses: Retroviral Vectors Carrying the Hygromycin Resistance–Encoding Gene", Gene 170:255–259.

Bergemann, J. et al., 1995, "Excision of Specific DNA–Sequences from Integrated Retroviral Vectors via Site–Specific Recombination", Nucl. Acids Res. 23:4451–4456.

Casini, T. and Graf, T., 1995, "Bicistronic Retroviral Vector Reveals Capacity of v–erbA to Induce Erythroleukemia and to Co–Operate with v–myb", Oncogene 11:1019–1026.

(List continued on next page.)

Primary Examiner—Nancy Degen
Assistant Examiner—Sean McGarry
Attorney, Agent, or Firm—Matthew P. Vincent; Diana M. Steel; Foley, Hoag & Eliot, LLP

[57] ABSTRACT

The present invention relates to methods and compositions for the elucidation of mammalian gene function. Specifically, the present invention relates to methods and compositions for improved mammalian complementation screening, functional inactivation of specific essential or non-essential mammalian genes, and identification of mammalian genes which are modulated in response to specific stimuli.

In particular, the compositions of the present invention include, but are not limited to, replication-deficient retroviral vectors, libraries comprising such vectors, retroviral particles produced by such vectors in conjunction with retroviral packaging cell lines, integrated provirus sequences derived from the retroviral particles of the invention and circularized provirus sequences which have been excised from the integrated provirus sequences of the invention. The compositions of the present invention further include novel retroviral packaging cell lines.

60 Claims, 9 Drawing Sheets pMaRX II

OTHER PUBLICATIONS

Gunnery, S. Mathews, M., 1995, "Functional mRNA Be Generated by RNA Polymerase III", Mol. Cell. Biol. 15:3597–3607.

Hsieh, C. et al., 1995, "Improved Gene Expression by a Modified Bicistronic Retroviral Vector", Biochem. Biophys. Res. Comm. 214:910–917.

Meyer, K. et al., 1995, "Interaction of Eukaryotic Initiation Factor eIF–4B with a Picornavirus Internal Translation Initiation Site", J. Virol. 69:2819–2824.

Price, J. et al., 1995, "The Expression of Functional Genes in the Rodent Nervous System with Dual–Expressing Retroviral Vectors Encoding an IRES Sequence", J. Cell. Biochem. Suppl O (21A):413.

Shah, D. et al., 1995, "Dissection of the Core and Auxiliary Sequences in the Vegetative Replication Origin of Promiscuous Plasmid RK2", J. Mol. Biol. 254:608–622.

Sugimoto, Y. et al., 1995, "Co–Expression of a Multidrug Resistance Gene (MDR1) and HSV–TK Gene in a Bicistronic Retroviral Vector pHa–MDR–IRES–TK Allows Selective Killing of MDR1–transduced Human Tumor Transplanted in Nude Mice", Proc. Amer. Assoc. for Cancer Res. 36:413.

Sugimoto, Y. et al., 1995, "Retroviral Coexpression of a Multidrug Resistance Gene (MDR1) and Human $\alpha$–Galactosidase A for Gene Therapy of Fabry Disease", Hum. Gene Ther. 6:905–915.

Vagner, S. et al., 1995, "Alternative Translation Initiation of the Moloney Murine Leukemia Virus mRNA Controlled by Internal Ribosome Entry Involving the p57/PTB Splicing Factor", J. Biol. Chem. 270:20376–20383.

Vile, R. and Russell, S., 1995, "Retroviruses as Vectors", Brit. Med. Bull. 51:12–30.

Whitehead, I. et al. 1995, "Expression Cloning of Oncogenes by Retroviral Transfer of cDNA Libraries", Mol. Cell. Biol. 15:704–710.

Whitehead, I. et al., 1995, "Retroviral Transduction and Oncogenic Selection of a cDNA Encoding Dbs, a Homolog of the Dbl Guanine Nucleotide Exchange Factor", Oncogene 10:713–721.

Whitehead, I. et al., 1995, "Retroviral–Mediated Expression Cloning of a Novel Oncogene with Structural Similarities to the CDC24 Family of Guanine Nucleotide Exchange Factors", J. Cell. Biochem. Suppl. O (19A):45.

Whitehead, I. et al., 1995, "Expression Cloning of Ifc, a Novel Oncogene with Structural Similarities to Guanine Nucleotide Exchange Factors and to the Regulatory Region of Protein Kinase C", J. Biol. Chem. 270:18388–18395.

Bernard, P. et al., 1994, "Positive–Selection Vectors Using the F Plasmid ccdB Killer Gene", Gene 148:71–74.

Qin, M et al., 1994, Cre Recombinase–Mediated Site–Specific Recombination Between Plant Chromosomes, Proc. Natl. Acad. Sci. USA 91:1706–1710.

Rayner, J. and Gonda, T., 1994, "A Simple and Efficient Procedure for Generating Stable Expression Libraries by cDNA Cloning in a Retroviral Vector", Mol. Cell. Biol. 14:880–887.

Scheper, G. ., 1994, "Binding of Eukaryotic Initiation tor–2 and trans–Acting Factors to the 5' Untranslated Region of Encephalomyocarditis Virus RNA", Biochimie 76:801–809.

Soares, M. et al., 1994, "Construction and Characterization of a Normalized cDNA Library", Proc. Natl. Acad. Sci. USA 91:9228–9232.

Sugimoto, Y. et al., 1994, "Efficient Expression of Drug––Selectable Genes in Retroviral Vectors Under Control of an Internal Ribosome Entry Site", Bio/Technology 12:694–698.

Tramontano, A. et al., 1994, "The Making of the Minibody: An Engineered $\beta$–Protein for the Display of Conformationally Constrained Peptides", J. Mol. Recognition 7:9–24.

Palmer, T. et al., 1993, "Efficient Expression of a Protein Coding Gene Under the Control of an RNA Polymerase I Promoter", Nucl. Acids Res. 21:3451–3457.

Pear, W. et al., 1993, "Production of High Titer Helper–Free Retroviruses by Transient Transfection", Proc. Nat'l. Acad. Sci USA 90:8392–8396.

Haller, A. and Semler, B., 1992, "Linker Scanning Mutagenesis of the Internal Ribosome Entry Site of Poliovirus RNA", J. Virol. 66:5075–5086.

Morgan, R. et al., 1992, "Retroviral Vectors Containing Putative Internal Ribosome Entry Sites: Development of a Polycistronic Gene Transfer System and Applications to Human Gene Therapy", Nucl. Acids Res. 20:1293–1299.

Rice, G. et al., 1992, "Random PCR Mutagenesis Screening of Secreted Proteins by Direct Expression in Mammalian Cells", Proc. Natl. Acad. Sci USA 89:5467–5471.

Cook, R. et al., 1991, "Retrotransposon Gene Engineering", Bio/Technology 9:748–751.

Ghattas, I. et al., 1991, "The Encephalomyocarditis Virus Internal Ribosome Entry Site Allows Efficient Coexpression of Two Genes From a Recombinant Provirus in Cultured Cells and Embryos", Mol. Cell. Biol. 11:5848–5859.

Jorgensen, P. et al., 1991, "Tagging the Genome of the Murine Leukemia Retrovirus SL3–3 by a Bacterial Iac Operator Sequence", Gene 109:243–248.

McLachlin, J. et al., 1990, "Retroviral–Mediated Gene Transfer", Prog. Nucl. Acid Res. and Mol. Biol. 38:91–135.

Morgenstern, J. and Land, H., 1990, "Advanced Mammalian Gene Transfer: High Titre Retroviral Vectors with Multiple Drug Selection Markers and a Complementary Helper–Free Packaging Cell Line", Nucl. Acids Res. 18:3587–3596.

Ott, D. et al., 1990, "Sequence Analysis of Amphotropic and 10A1 Murine Leukemia Viruses: Close Relationship to Mink Cell Focus–Inducing Viruses", J. Virol. 64:757–766.

Tolstoshev, P. and Anderson, W., 1990, "Gene Expression Using Retroviral Vectors", Curr. Opinion in Biotech. 1:55–61.

Danos, O. and Mulligan, R., 1988, "Safe and Efficient Generation of Recombinant Retroviruses with Amphotrophic and Ectrophic Host Ranges", Proc. Natl. Acad. Sci. USA 85:6460–6464.

Eglitis, M. and Anderson, W., 1988, "Retroviral Vectors Introduction of Genes into Mammalian Cells", BioTechniques 6:608–614.

Fabry, S. et al., 1988, "Expression of the Glyceraldehyde–3–Phosphate Dehydrogenase Gene from the Extremely Thermophilic Archaebacterium *Methanothermus fervidus* in *E. coli*", FEBS Lett. 237:213–217.

Jang, S. et al., 1988, "A Segment of the 5' Nontranslated Region of Encephalomyocarditis Virus RNA Directs Internal Entry of Ribosomes During In Vitro Translation", J. Virol. 62:2636–2643.

Markowitz, D. et al., 1988, "Construction and Use of a Safe and Efficient Amphotrophic Packaging Cell Line", Virology 167:400–406.

Markowitz, D. et al., 1988, "A Safe Packaging Line for Gene Transfer; Separating Viral Genes on Two Different Plasmids", J. Virol. 62:1120–1124.

Hoess, R. et al., 1986, "The Role of the IoxP Spacer Region in P1 Site–Specific Recombination", Nucl. Acids. Res. 14:2287–2300.

Cone, R. and Mulligan, R., 1984, "High–Efficiency Gene Transfer into Mammalian Cells: Generation of Helper–Free Recombinant Retrovirus with Broad Mammalian Host Range", Proc. Natl. Acad. Sci. USA 81:6349–6353 (as reprinted in Milestones in Biotechnology, pp. 420–424).

Mann, R. et al., 1983, "Construction of a Retrovirus Packaging Mutant and Its Use to Produce Helper–Free Defective Retrovirus", Cell 33:153–159.

Gabrielson et al "Magnetic DNA AFF Purification of Yeast Transcription Factor $\pi$—A New Purification Principle for the Ultrarand Isolation of Near Homogous Factor." Nucleic Acids Research. vol. 17(15):6253–5267, 1989.

MODIFIED RETROVIRAL VECTORS

GOVERNMENT FUNDING

This invention was partially funded by NIH Grant No. 1RO1CA68040, 5RO1CA63518, and by Department of the Army Grant No. DAMD17-1-6053; the government has certain rights to the invention.

1. INTRODUCTION

The present invention relates to methods and compositions for the elucidation of mammalian gene function. Specifically, the present invention relates to methods and compositions for improved mammalian complementation screening, functional inactivation of specific essential or non-essential mammalian genes, and identification of mammalian genes which are modulated in response to specific stimuli.

2. BACKGROUND

In yeast, methods have been devised by which the problems of gene isolation and discovery of gene function can be addressed efficiently. For example, in yeast it is possible to isolate genes via their ability to complement specific phenotypes. Further, in yeast, targeted insertional mutagenesis techniques can be used in yeast to inactivate or "knock out" a gene's activity. In mammalian systems, however, such methods are, in practical terms, lacking, which has made the elucidation of mammalian gene function a very difficult task.

For example, with respect to gene inactivation techniques in mammalian cells, the fact that mammalian cells are diploid and have complex genomes cause insertional mutagenesis techniques in mammalian systems to be a laborious, time-consuming and lengthy process.

Further, a major barrier to the development of such capabilities as complementation screening in mammalian cells has been that conventional techniques yield gene transfer efficiencies in most cells (0.01%–0.1%) that make screening of high complexity libraries impractical. While reports indicate that recombinant, replication deficient retroviruses can make possible increased gene transfer efficiencies in mammalian cells (Rayner & Gonda, 1994, Mol. Cell. Biol. 14:880–887; Whitehead et al., 1995, Mol. Cell. Biol. 15:704–710), retroviral-based functional mammalian cloning systems are inconvenient and have, thus far, failed to achieve widespread use.

The lack of convenience and impracticality of current retroviral-based cloning systems include, for example, the fact that the production of high complexity libraries has been limited by the low transfection efficiency of known retroviral packaging cell lines. Furthermore, no system has provided for routine, easy recovery of integrated retroviral proviruses from the genomes of positive clones. For example, in currently used systems the recovery of retrovirus inserts may be accomplished by polymerase chain reaction (PCR) techniques, however this is quite time consuming and variable for different inserts. Furthermore, with the use of PCR, additional cloning steps are still required to generate viral vectors for subsequent screening. Additionally, no mechanism has been available for distinguishing revertants from provirus-dependent rescues, a major source of false positives.

3. SUMMARY OF THE INVENTION

The present invention relates to methods and compositions for the elucidation of mammalian gene function. Specifically, the present invention relates to methods and compositions for improved mammalian complementation screening, functional inactivation of specific essential or non-essential mammalian genes, and identification of mammalian genes which are modulated in response to specific stimuli.

In particular, the compositions of the present invention include, but are not limited to, replication-deficient retroviral vectors, libraries comprising such vectors, retroviral particles produced by such vectors in conjunction with retroviral packaging cell lines, integrated provirus sequences derived from the retroviral particles of the invention and circularized provirus sequences which have been excised from the integrated provirus sequences of the invention. The compositions of the present invention further include novel retroviral packaging cell lines.

The methods of the present invention include, but are not limited to, methods for the identification and isolation of nucleic acid molecules based upon their ability to complement a mammalian cellular phenotype, antisense-based methods for the identification and isolation of nucleic acid sequences which inhibit the function of a mammalian gene, and gene trapping methods for the identification and isolation of mammalian genes which are modulated in response to specific stimuli.

4. BRIEF DESCRIPTION OF THE FIGURES

FIG. 1. The arrangement of DNA elements that comprise the replication-defective retroviral vector, MaRXII. psi denotes the packaging signal.

Figure 2:
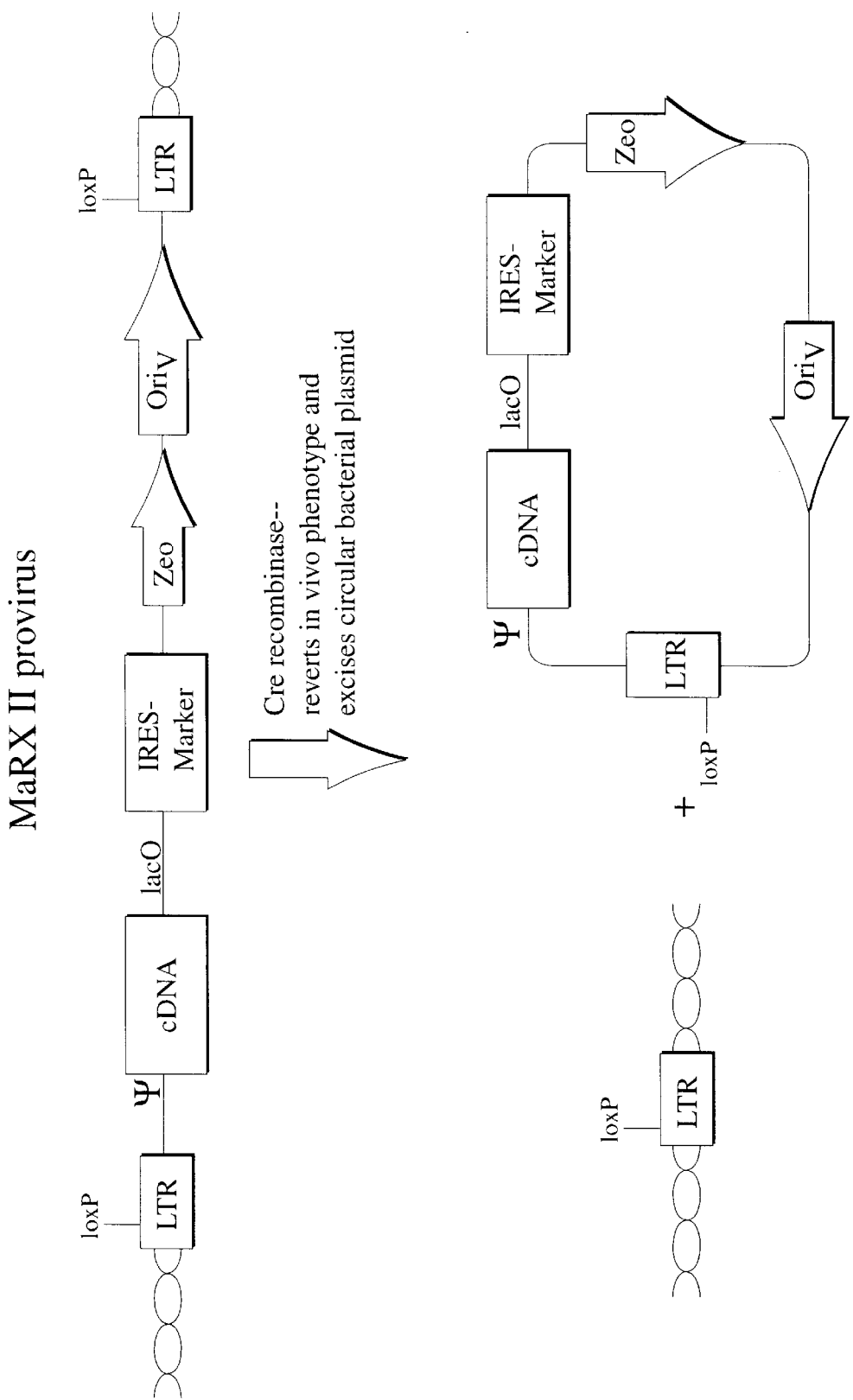

FIG. 2. Diagramatic representation of the cleavage of the loxP sites with Cre recombinase enzyme, yielding an excised provirus which upon excision, becomes circularized.

Figure 3:
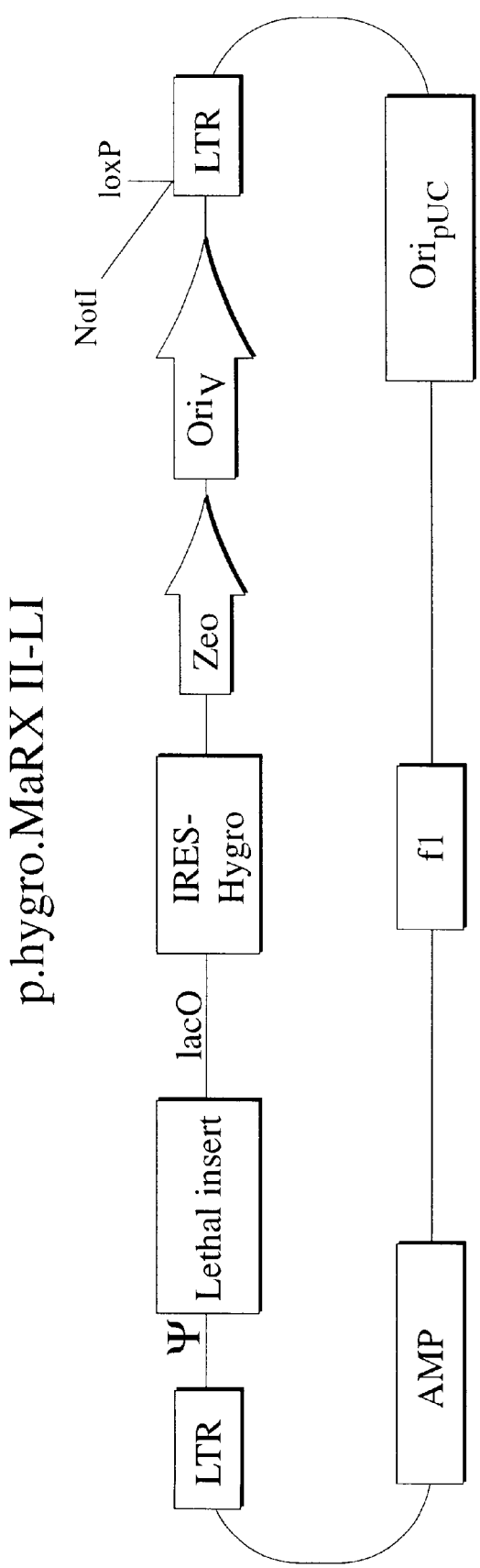

FIG. 3. The arrangement of DNA elements that comprise the retroviral vector for sense complementation screening, p.hygro.MaRXII-LI.

Figure 4:
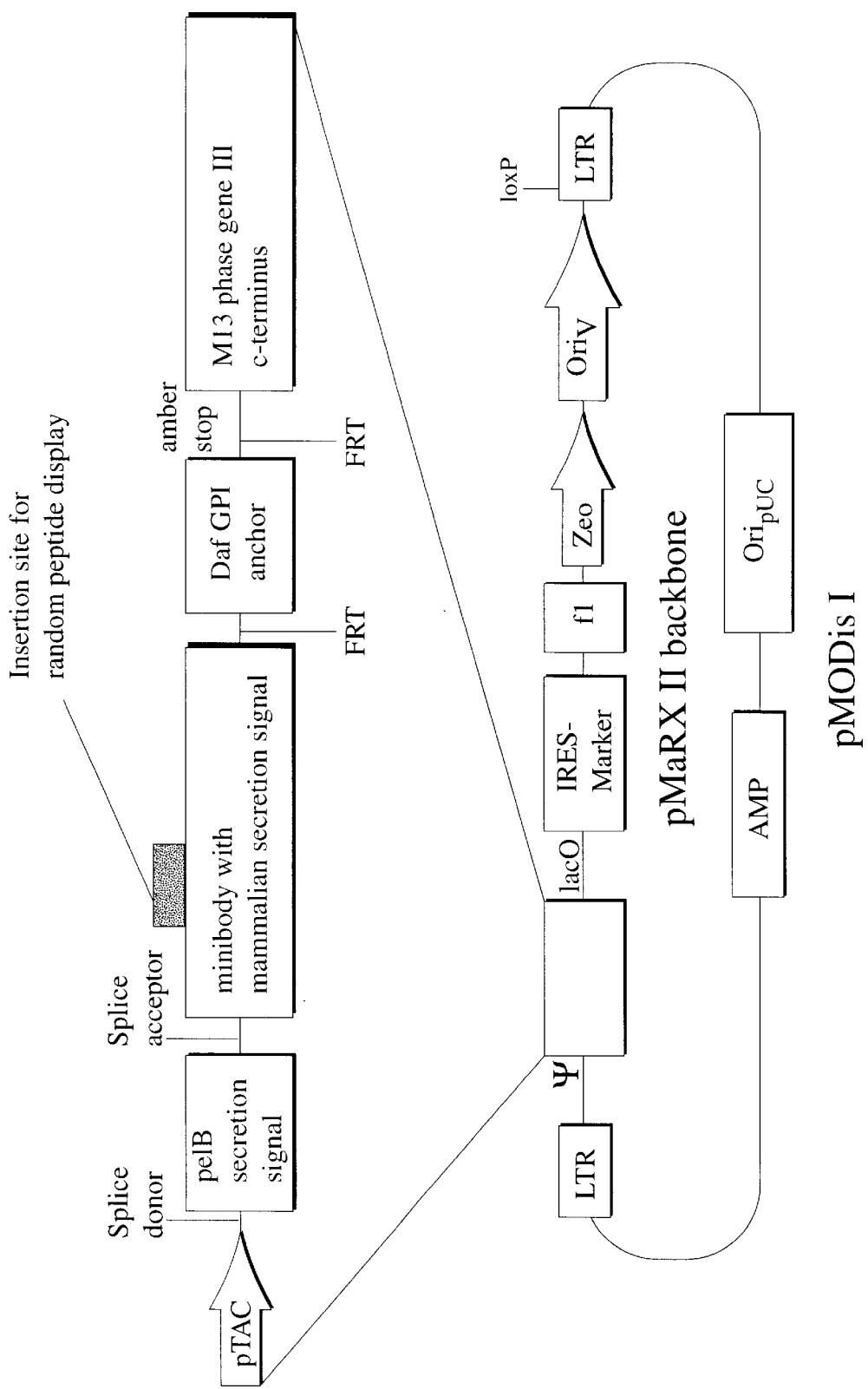

FIG. 4. The arrangement of DNA elements that comprise a retroviral vector for peptide display, pMODis-I.

Figure 5:
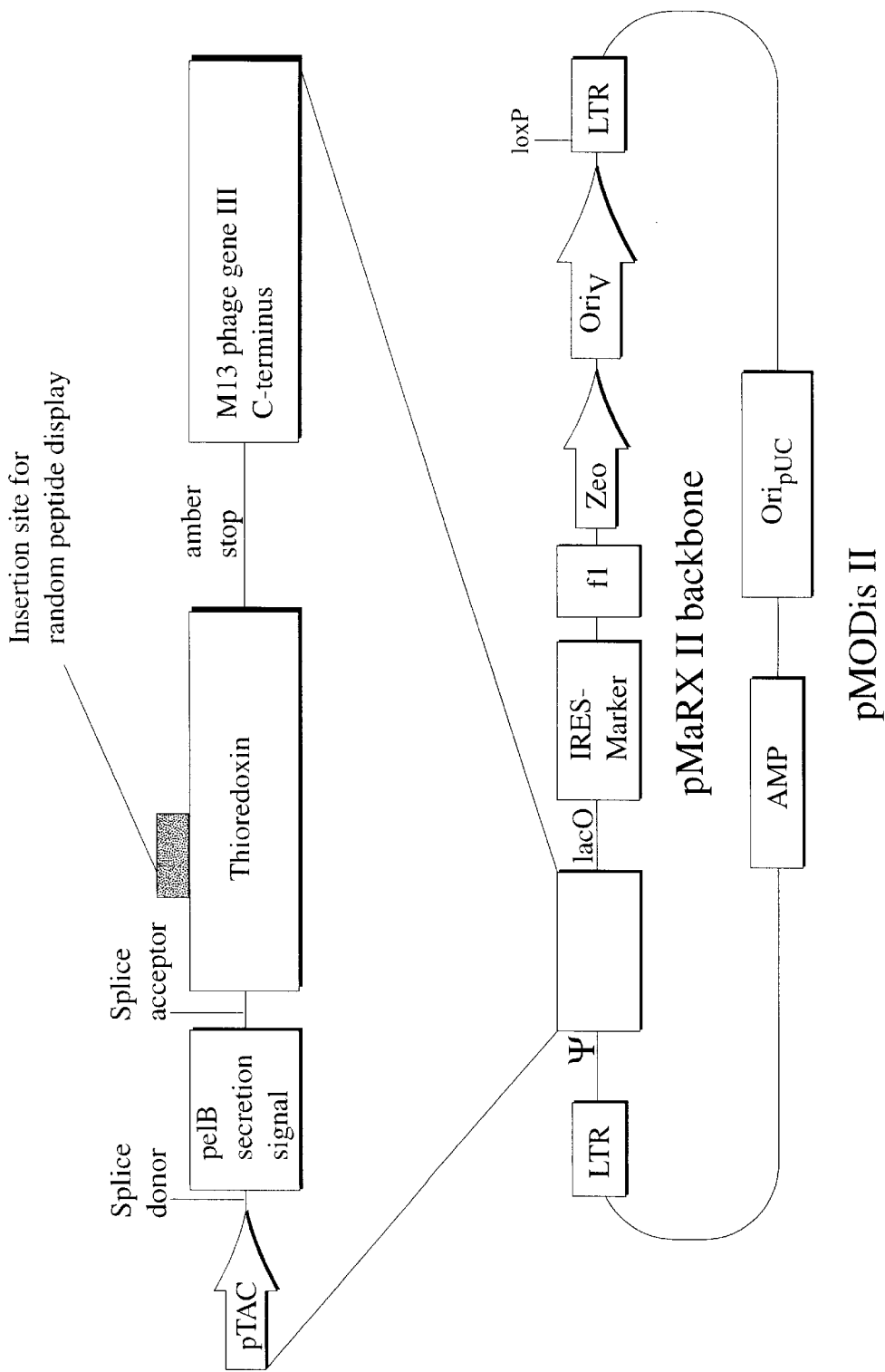

FIG. 5. The arrangement of DNA elements that comprise a retroviral vector for peptide display, pMODis-II.

Figure 6:
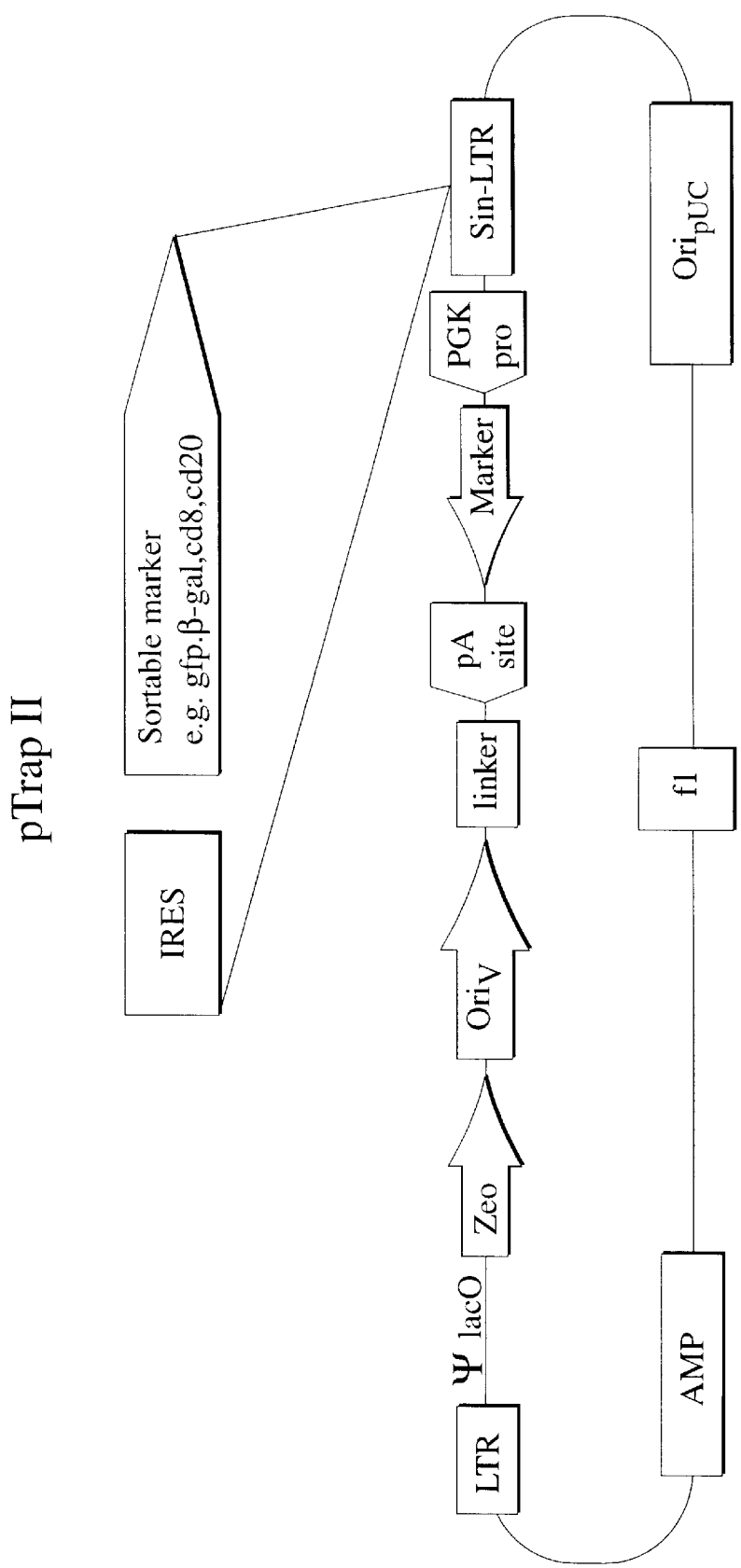

FIG. 6. The arrangement of DNA elements that comprise the retroviral vector for gene trapping, pTRAPII.

Figure 7:
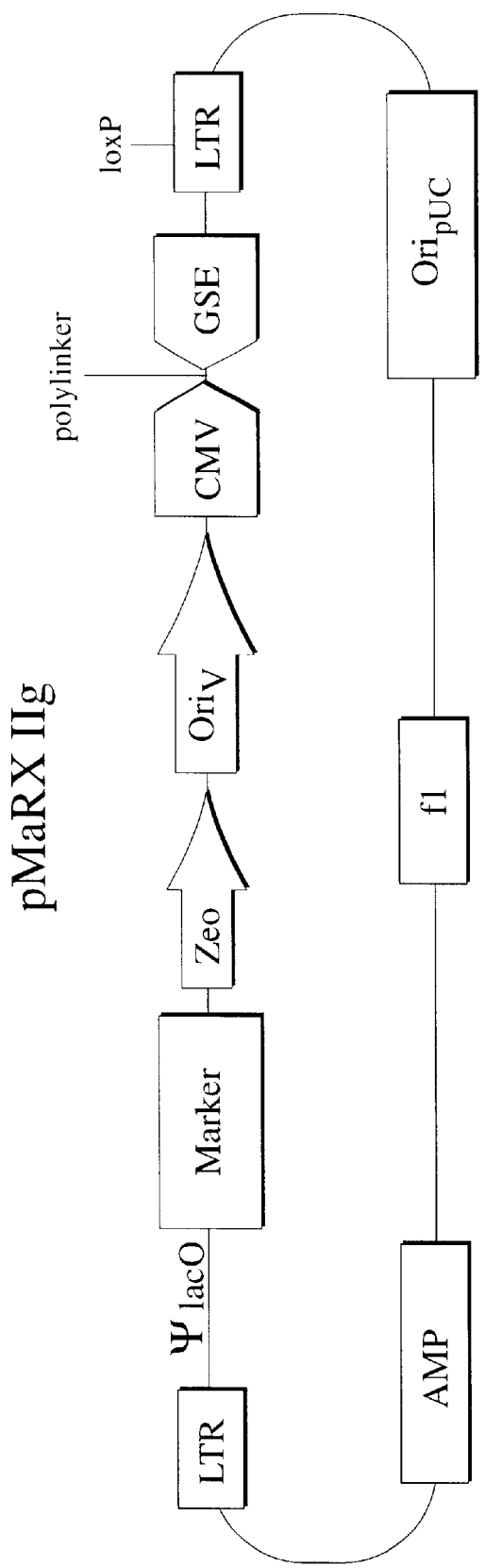

FIG. 7. The arrangement of DNA elements that comprise a retroviral vector for antisense complementation screening, pMaRXIIg.

Figure 8:
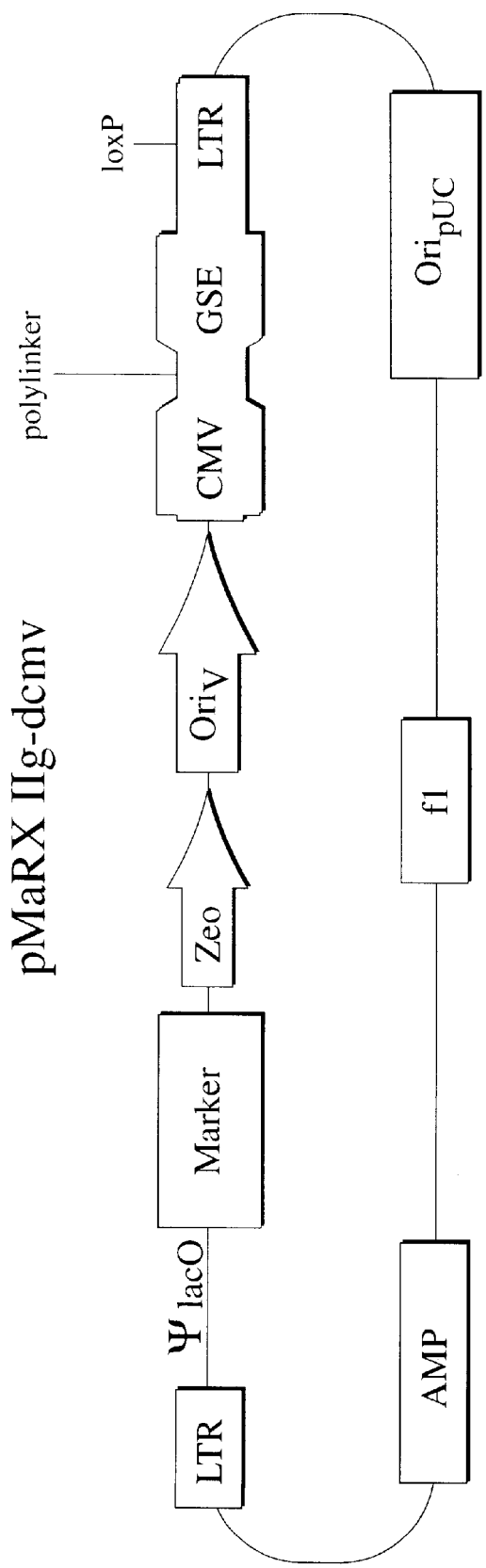

FIG. 8. The arrangement of DNA elements that comprise a retroviral vector for antisense complementation screening, pMaRXIIg-demV.

Figure 9:
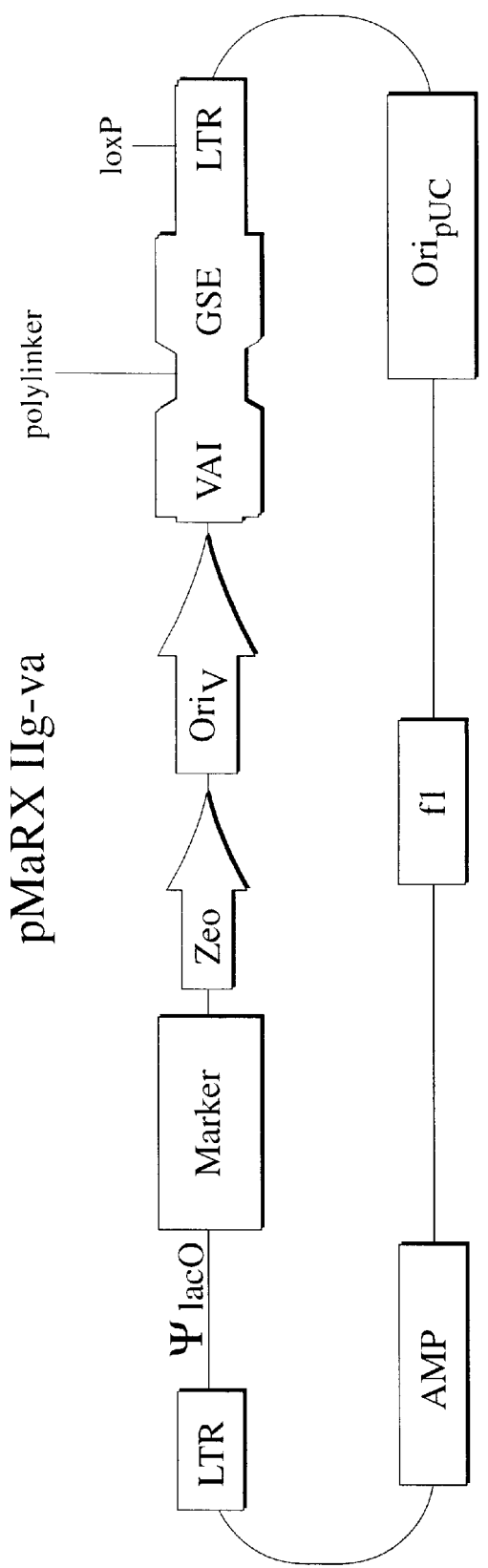

FIG. 9. The arrangement of DNA elements that comprise a retroviral vector for antisense complementation screening, pMaRXIIg-va.

5. DETAILED DESCRIPTION OF THE INVENTION

Described herein are, first, the compositions of the present invention. Such compositions include, but are not limited to, replication-deficient retroviral vectors, libraries comprising such vectors, retroviral particles produced by such vectors in conjunction with retroviral packaging cell lines, integrated provirus sequences derived from the retroviral particles of the invention and circularized provirus sequences which have been excised from the integrated provirus sequences of the invention. The compositions of the present invention further include novel retroviral packaging cell lines.

Second, the methods of the invention are described. Such methods include, but are not limited to, methods for the identification and isolation of nucleic acid molecules which complement a mammalian cellular phenotype, antisense-based methods for the identification and isolation of nucleic acid sequences which inhibit the function of a mammalian gene, and gene trapping methods for the identification and isolation of mammalian genes which are modulated in response to specific stimuli.

The methods of the present invention also include, but are not limited to, methods for the identification and isolation of peptide sequences by complementation type screens using vectors capable of displaying random synthetic peptide sequences which will interact with proteins important for a particular function. This interaction will result in the elaboration of selectable phenotype.

5.1 COMPLEMENTATION SCREENING RETROVIRAL VECTORS

Replication-deficient retroviral vectors compositions are described herein which comprise a combination of features that make possible, for the first time, practical, efficient complementation screening in mammalian cells.

Such retroviral vectors comprise a replication-deficient retroviral genome containing a polycistronic message cassette, a proviral excision element for excising retroviral provirus from the genome of a recipient cell and a proviral recovery element for recovering excised provirus from a complex mixture of nucleic acid. The vectors are designed to facilitate expression of cDNA or genomic DNA (gDNA) sequences in mammalian cells.

The retroviral vectors further contain the following elements: (a) a 5' retroviral long terminal repeat (5' LTR); (b) a 3' retroviral long terminal repeat (3' LTR); (c) a packaging signal; (d) a bacterial origin of replication; and (e) a bacterial selectable marker. The polycistronic message cassette, proviral recovery element, packaging signal, bacterial origin of replication and bacterial selectable marker are located within the retroviral vector at positions between the 5' LTR and the 3' LTR. The proviral excision element, as discussed below, is located within the 3' LTR. In the alternative, the proviral excision element may also be located within the retroviral vector. However, this is not preferred, since the recovered plasmid could not be used to generate a virus directly.

The retroviral vectors' polycistronic message cassette makes possible a selection scheme which directly links expression of a selectable marker to transcription of a cDNA or gDNA sequence. Such a polycistronic message cassette can comprise, in one embodiment, from 5' to 3', the following elements: a nucleotide polylinker, an internal ribosome entry site and a mammalian selectable marker. The polycistronic cassette is situated within the retroviral vector between the 5' LTR and the 3' LTR at a position such that transcription from the 5' LTR promoter transcribes the polycistronic message cassette. The transcription of the polycistronic message cassette may also be driven by an internal cytomegalovirus (CMV) promoter or an inducible promoter, which may be preferable depending on the screenings. The polycistronic message cassette can further comprise a cDNA or genomic DNA (gDNA) sequence operatively associated within the polylinker.

Internal ribosome entry site sequences are well known to those of skill in the art and can comprise, for example, internal ribosome entry sites derived from foot and mouth disease virus (FDV), encephalomyocarditis virus, poliovirus and RDV (Scheper, 1994, *Biochemic* 76: 801–809; Meyer, 1995, *J. Virol.* 69: 2819–2824; Jang, 1988, *J. Virol.* 62: 2636–2643; Haller, 1992, *J. Virol.* 66: 5075–5086).

Any mammalian selectable marker can be utilized as the polycistronic message cassette mammalian selectable marker. Such mammalian selectable markers are well known to those of skill in the art and can include, but are not limited to, kanamycin/G418, hygromycin B or mycophenolic acid resistance markers.

The retroviral vectors' proviral excision element allows for excision of retroviral provirus (see below) from the genome of a recipient cell. The element comprises a nucleotide sequence which is specifically recognized by a recombinase enzyme. The recombinase enzyme cleaves nucleic acid at its site of recognition in such a manner that excision via recombinase action leads to circularization of the excised nucleic acid molecules.

In a preferred embodiment, the recombinase recognition site is located within the 3' LTR at a position which is duplicated upon integration of the provirus. This results in a provirus that is flanked by recombinase sites.

In another preferred embodiment, the proviral excision element comprises a loxP recombination site, which is cleavable by a Cre recombinase enzyme. Contacting Cre recombinase to an integrated provirus derived from the retroviral vector results in excision of the provirus nucleic acid. In the alternative, a mutant lox P recombination site any be used (e.g., lox P511 (Hoess et al., 1986, Nucleic Acids Research 14:2287–2300)) that can only recombine with an identical mutant site.

In yet another preferred embodiment, an frt recombination site, which is cleavable by a flp recombinase enzyme, is utilized in conjunction with flp recombinase enzyme, as described above for the loxP/Cre embodiment. In yet an alternative embodiment, a rare-cutting restriction enzyme (e.g., Not 1) may be used in place of the recombinase site. The recovered DNA would be digested with Not 1 and then recircularized with ligase. In this embodiment, the Not 1 site is included in the vector next to loxP.

In the complementation screening system of the invention, described below, such excision systems can also serve to discriminate revertants from virus-dependent rescue events.

The retroviral vectors' proviral recovery element allows for recovery of excised provirus from a complex mixture of nucleic acid, thus allowing for the selective recovery and excision of provirus from a recipient cell genome. The proviral recovery element comprises a nucleic acid sequence which corresponds to the nucleic acid portion of a high affinity binding nucleic acid/protein pair.

The nucleic acid can include, but is not limited to, a nucleic acid which binds with high affinity to a lac repressor, tet repressor or lambda repressor protein. For example, in one embodiment, the proviral recovery element comprises a lac operator nucleic acid sequence, which binds to a lac repressor peptide sequence. Such a proviral recovery element can be affinity-purified using lac repressor bound to a matrix (e.g., magnetic beads or sepharose). An excised provirus derived from the retroviral vectors of the invention also contains the retroviral recovery element and can be affinity purified.

The 5' LTR comprises a promoter, including but not limited to an LTR promoter, an R region, a U5 region and a primer binding site, in that order. Nucleotide sequences of these LTR elements are well known to those of skill in the art.

The 3' LTR comprises a U3 region which comprises the proviral excision element, a promoter, an R region and a polyadenylation signal. Nucleotide sequences of such elements are well known to those of skill in the art.

The bacterial origin of replication (Ori) utilized is preferably one which does not adversely affect viral production or gene expression in infected cells. As such, it is preferable that the bacterial Ori is a non-pUC bacterial Ori relative (e.g., pUC, colEI, pSC101, p15A and the like). Further, it is preferable that the bacterial Ori exhibit less than 90% overall nucleotide similarity to the pUC bacterial Ori. In a preferred embodiment, the bacterial origin of replication is a RK2 OriV or f1 phage Ori.

Any bacterial selectable marker can be utilized. Bacterial selectable markers are well known to those of skill in the art and can include, but are not limited to, kanamycin/G418, zeocin, actinomycin, ampicillin, gentamycin, tetracycline, chloramphenicol or penicillin resistance markers.

The retroviral vectors can further comprise a lethal stuffer fragment which can be utilized to select for vectors containing cDNA or gDNA inserts during, for example, construction of libraries comprising the retroviral vectors of the invention. Lethal stuffer fragments are well known to those of skill in the art (see, e.g., Bernord et al., 1994, Gene 148:71–74, which is incorporated herein by reference in its entirety). A lethal stuffer fragment contains a gene sequence whose expression conditionally inhibits cellular growth.

In one embodiment, the stuffer fragment is present in the retroviral vectors of the invention within the polycistronic message cassette polylinker such that insertion of a cDNA or gDNA sequence into the polylinker replaces the stuffer fragment. Alternatively, the polycistronic message cassette polylinker is located within the lethal stuffer fragment coding sequence such that, upon insertion of a cDNA or gDNA sequence into the polylinker, the lethal stuffer fragment coding region is disrupted. Each of these embodiments can be utilized to counter select retroviral vectors not containing polylinker insertions.

The retroviral vectors can further comprise a single-stranded replication origin, preferably an f1 single-stranded replication origin. The single-stranded replication origin allows for the production of normalized single-stranded retroviral libraries derived from the retroviral vectors of the invention. A normalized library is one constructed in a manner that increases the relative frequency of occurrence of rare clones while decreasing simultaneously the relative frequency of the occurrence of abundant clones. For teaching regarding the production of normalized libraries, see, e.g., Soares et al. (Soares, M. B. et al., 1994, Proc. Natl. Acad. Sci. USA 91:9228–9232, which is incorporated herein by reference in its entirety). Alternative normalization procedures based upon biotinylated nucleotides may also be utilized.

5.2 ANTISENSE-GENETIC SUPPRESSOR ELEMENT VECTORS

Described herein are genetic suppressor element (GSE)-producing, replication-deficient retroviral vectors. Such vectors are designed to facilitate the expression of antisense GSE single-stranded nucleic acid sequences in mammalian cells, and can, for example, be utilized in conjunction with the antisense-based functional gene inactivation methods of the invention.

The GSE-producing retroviral vectors of the invention can comprise a replication-deficient retroviral genome containing a proviral excision element, a proviral recovery element and a genetic suppressor element (GSE) cassette.

The GSE-producing retroviral vectors can further comprise, (a) a 5' LTR; (b) a 3' LTR; (c) a bacterial Ori; (d) a mammalian selectable marker; (e) a bacterial selectable marker; and (f) a packaging signal.

The proviral recovery element, GSE cassette, bacterial Ori, mammalian selectable marker and bacterial selectable marker are located between the 5' LTR and the 3' LTR. The proviral excision element is located within the 3' LTR. The proviral excision element can also flank the functional cassette without being present in the 3' LTR.

The 5' LTR, 3' LTR, proviral excision element, bacterial selectable marker, mammalian selectable marker and proviral recovery element are as described in Section 5.1, above.

Each of the GSE cassette embodiments described below can further comprise a sense or antisense cDNA or gDNA fragment or full length sequence operatively associated within the polylinker.

The GSE cassette can, for example, comprise, from 5' to 3': (a) a transcriptional regulatory sequence; (b) a polylinker; and (c) polyadenylation signal. In one embodiment, the GSE cassette polyadenylation signal is located within the 3' retroviral long terminal repeat.

Alternatively, the GSE cassette can comprise, from 5' to 3': (a) a transcriptional regulatory sequence; (b) a polylinker; (c) a cis-acting ribozyme sequence; (d) an internal ribosome entry site; (e) the mammalian selectable marker; and (f) a polyadenylation signal.

In a further alternative, a sense GSE can be constructed, in which case the GSE cassette can further comprise a polylinker containing a Kozak consensus methionine in front of the sense-orientation fragments to create a "domain library" for domain and fragment expression.

In such an embodiment, transcription from the transcriptional regulatory sequence produces a bifunctional transcript. The first half (i.e., the portion upstream of the ribozyme sequence) is likely to remain nuclear and represents the GSE. The portion downstream of the ribozyme sequence (i.e., the portion containing the selectable marker) is transported to the cytoplasm and translated. Such a bicistronic configuration, therefore, directly links selection for the selectable marker to expression of the GSE.

In another alternative, the GSE cassette can comprise, from 5' to 3': (a) an RNA polymerase III transcriptional regulatory sequence; (b) a polylinker; (c) a transcriptional termination sequence. In a particular embodiment, the transcriptional regulatory sequence and transcriptional termination sequence are adenovirus Ad2 VA RNAI transcriptional regulatory and termination sequences.

5.3 VECTORS DISPLAYING RANDOM PEPTIDE SEQUENCES

Described herein are vectors useful for the display of constrained and unconstrained random peptide sequences. Such vectors are designed to facilitate the selection and identification of random peptide sequences that bind to a protein of interest.

The vectors displaying random peptide sequences of the present invention can comprise, (a) a splice donor site or a LoxP site (e.g., LoxP511 site); (b) a bacterial promoter (e.g., pTac) and a shine-delgarno sequence; (c) a pel B secretion signal for targeting fusion peptides to the periplasm; (d) a splice-acceptor site or another LoxP511 site (LoxP511 sites will recombine with each other, but not with the LoxP site in the 3' LTR); (e) a peptide display cassette or vehicle; (f) an amber stop codon; (g) the M13 bacteriophage gene 111 protein C-terminus (amino acids 198–406); and optionally the vector may also comprise a flexible polyglycine linker.

A peptide display cassette or vehicle consists of a vector protein, either natural or synthetic into which a polylinker has been inserted into one flexible loop of the natural or synthetic protein. A library of random oligonucleotides encoding random peptides may be inserted into the polylinker, so that the peptides are expressed on the cell surface.

The display vehicle of the vector may be, but is not limited to, thioredoxin for intracellular peptide display in mammalian cells (Colas et al., 1996, Nature 380:548–550) or may be a minibody (Tramonteno, 1994, *J. Mol. Recognit.* 7:9–24) for the display of peptides on the mammalian cell surface. Each of these would contain a polylinker for the insertion of a library of random oligonucleotides encoding random peptides at the positions specified above. In an alternative embodiment, the display vehicle may be extracellular, in this case the minibody could be preceded by a secretion signal and followed by a membrane anchor, such as the one encoded by the last 37 amino acids of DAF-1 (Rice et al., 1992, Proc. Natl. Acad. Sci. 89:5467–5471). This could be flanked by recombinase sites (e.g., FRT sites) to allow the production of secreted proteins following passage of the library through a recombinase expressing host.

In one embodiment of the present invention, these cassettes would reside at the position normally occupied by the cDNA in the sense-expression vectors described above. In an amber suppressor strain of bacteria and in the presence of helper phage, these vectors would produce a relatively conventional phage display library which could be used exactly as has been previously described for conventional phage display vectors. Recovered phage that display affinity for the selected target would be used to infect bacterial hosts of the appropriate genotype (i.e., expressing the desired recombinases depending upon the cassettes that must be removed for a particular application). For example for an intracellular peptide display, any bacterial host would be appropriate (provided that splice sites are used to remove pelB in the mammalian host). For a secreted display, the minibody vector would be passed through bacterial cells that catalyze the removal of the DAF anchor sequence. Plasmids prepared from these bacterial hosts are used to produce virus for assay of specific phenotypes in mammalian cells.

In some cases, if the target is unknown the phage display step could be skipped and the vectors could be used for intracellular or extracellular random peptide display directly. The advantage of these vectors over conventional approaches is their flexibility. The ability to functionally test the peptide sequence in mammalian cells without additional cloning or sequencing steps makes possible the use of much cruder binding targets (e.g., whole fixed cells) for phage display. This is made possible by the ability to do a rapid functional selection on the enriched pool of bound phages by conversion to retroviruses that can infect mammalian cells.

5.4 GENE TRAPPING VECTORS

Described herein are replication-deficient retroviral gene trapping vectors. Such gene trapping vectors contain reporter sequences which, when integrated into an expressed gene, "tag" the expressed gene, allowing for the monitoring of the gene's expression, for example, in response to a stimulus of interest. The gene trapping vectors of the invention can be used, for example, in conjunction with the gene trapping-based methods of the invention for the identification of mammalian genes which are modulated in response to specific stimuli.

The replication-deficient retroviral gene trapping vectors of the invention can comprise: (a) a 5' LTR; (b) a promoterless 3' LTR (a SIN LTR); (c) a bacterial Ori; (d) a bacterial selectable marker; (e) a selective nucleic acid recovery element for recovering nucleic acid containing a nucleic acid sequence from a complex mixture of nucleic acid; (f) a polylinker; (g) a mammalian selectable marker; and (h) a gene trapping cassette. In addition, those elements necessary to produce a high titer virus are required. Such elements are well known to those of skill in the art and contain, for example, a packaging signal.

The bacterial Ori, bacterial selectable marker, selective nucleic acid recovery element, polylinker, and mammalian selectable marker are located between the 5' LTR and the 3' LTR. The bacterial selectable marker and the bacterial Ori are located in close operative association in order to facilitate nucleic acid recovery, as described below. The gene trapping cassette element is located within the 3' LTR.

The 5' LTR, bacterial selectable marker and mammalian selectable marker are as described in Section 5.1, above. The selective nucleic acid recovery element is as the proviral recovery element described, above, in Section 5.1, above.

The 3' LTR contains the gene trapping cassette and lacks a functional LTR transcriptional promoter.

The gene trapping cassette can comprise from 5' to 3': (a) a nucleic acid sequence encoding at least one stop codon in each reading frame; (b) an internal ribosome entry site; and (c) a reporter sequence. The gene trapping cassette can further comprise, upstream of the stop codon sequences, a transcriptional splice acceptor nucleic acid sequence.

The inclusion of the IRES sequence in the gene trapping vectors of the present invention offers a key improvement over conventional gene trapping vectors. The IRES sequence allows the vector to land anywhere in the mature message to create a bicistronic transcript, this effectively increases the number of integration sites that will report promoters by a factor of at least 10.

5.5 RETROVIRAL VECTOR DERIVATIVES

Described herein are derivatives of the retroviral vectors of the invention, including libraries, retroviral particles, integrated proviruses and excised proviruses.

The compositions of the present invention further include libraries comprising a multiplicity of the retroviral vectors of the invention, said retroviral vectors further containing cDNA or gDNA sequences. A number of libraries may be used in accordance with the present invention, including but not limited to, normalized and non-normalized libraries for sense and antisense expression; libraries selected against specific chromosomes or regions of chromosomes (e.g., as comprised in YACs or BACs), which would be possible by the inclusion of the f1 origin; and libraries derived from any tissue source.

The compositions of the present invention still further include retrovirus particles derived from the retroviral vectors of the invention. Such retrovirus particles are produced by the transfection of the retrovirus vectors of the invention into retroviral packaging cell lines, including, but not limited to, the novel retroviral packaging cell lines of the invention.

The compositions of the invention additionally include provirus sequences derived from the retrovirus particles of the invention. The provirus sequences of the invention can be present in an integrated form within the genome of a recipient mammalian cell, or may be present in a free, circularized form.

An integrated provirus is produced upon infection of a mammalian recipient cell by a retrovirus particle of the invention, wherein the infection leads to the production and integration into the mammalian cell genome of the provirus nucleic acid sequence.

The circularized provirus sequences of the invention are generally produced upon excision of the integrated provirus from the recipient cell genome.

5.6 RETROVIRAL PACKAGING CELL LINES

Described herein are novel, stable retroviral packaging cell lines which efficiently package retroviral-derived nucleic acid into replication-deficient retroviral particles capable of infecting appropriate mammalian cells. Such packaging cell lines are produced by a novel method which directly links the expression of desirable viral proteins with expression of a selectable marker.

The retroviral packaging cell lines of the invention provide retroviral packaging functions as part of a polycistronic message which allowing direct selection for the expression of such viral functions and, further, makes possible a quantitative selection for the highest expression of desirable sequences.

Retroviral packaging functions comprise gag/pol and env packaging functions. gag and pol provide viral structural components and env functions to target virus to its receptor. Env function can comprise an envelope protein from any amphotropic, ecotrophic or xenotropic retrovirus, including but not limited to MuLV (such as, for example, an MuLV 4070A) or MoMuLV. Env can further comprise a coat protein from another virus (e.g., env can comprise a VSV G protein) or it can comprise any molecule that targets a specific cell surface receptor.

In one embodiment of such a method, a retroviral packaging cell line containing a tricistronic expression cassette is used as a founder line for selection of novel efficient, stable retroviral packaging cell lines. The tricistronic message cassette comprises a gene sequence important for efficient packaging of retroviral-derived nucleic acid into functional retroviral particles in operative association with a selectable marker and a quantifiable marker. The gene sequence, the selectable marker and the quantifiable marker are transcribed onto a single message whose expression is controlled by a single set of regulatory sequences. In such an embodiment, the gene sequence important for packaging can represent, for example, a gal/pol or an env gene sequence.

In an alternative embodiment, the retroviral packaging cell line contains a polycistronic expression cassette comprising at least two gene sequences important for efficient packaging of retroviral-derived nucleic acid into functional retroviral particles in operative association with a selectable marker and a quantifiable marker. The gene sequences, the selectable marker and the quantifiable marker are transcribed onto a single message whose expression is controlled by a single set of regulatory sequences. For example, in such an embodiment the gene sequences important for packaging can represent gag/pol and env gene sequences.

The polycistronic, such as, for example, tricistronic, message approach allows for a double selection of desirable packaging cell lines. First, selection for the selectable marker ensures that only those cells expressing the gene sequence important for packaging are selected for. Second, those cells exhibiting the highest level of quantifiable marker (and, therefore, exhibiting the highest level of expression of the gene sequence important for packaging) can be selected.

In a variation of the above embodiment, cell lines containing greater than one polycistronic, e.g., tricistronic, message cassette can be utilized. For example, one message cassette comprising a first gene sequence important for retroviral packaging, a first selectable marker and a first quantifiable marker can be utilized to select for the greatest expression of the first gene sequence, while a second message cassette comprising a second gene important for efficient retroviral packaging, a second selectable marker and a second quantifiable marker can be utilized to select for the greatest expression of the second gene sequence, thereby creating a packaging cell line which is optimized for both the first and the second gene sequences important for packaging.

The quantifiable marker is, for example, any marker that can be quantified by florescence activated cell sorting (FACS) methods. Such a quantifiable marker can include, but is not limited to, any cell surface marker, such as, for example, CD4, CD8 or CD20, in addition to any synthetic or foreign cell surface marker. Further, such a quantifiable marker can include an intracellular fluorescent marker, such as, for example, green fluorescent protein. Additionally, the quantifiable marker can include any other marker whose expression can be measured, such as, for example, a beta galactosidase marker.

The selectable marker chosen can include, for example, any selectable drug marker, including, but not limited to hygromycin, blasticidin, neomycin, puromycin, histidinol, zeocin and the like.

High level expression can be achieved by a variety of means well known to those of skill in the art. For example, expression of sequences encoding viral functions can be regulated and driven by regulatory sequences comprising inducible and strong promoters including, but not limited to, CMV promoters.

Alternatively, high copy numbers of polycistronic cassettes can be achieved via a variety of methods. For example, stable genomic insertion of high copy numbers of polycistronic cassettes can be obtained. In one method, extrachromosomal cassette copy number can first be achieved, followed by selection for stable high-copy number insertion. For example, extrachromosomal copy number can be increased via use of SV40 T antigen and SV40 origin of replication in conjunction with standard techniques well known to those of skill in the art.

High stable extrachromosomal cassette copy number can also be achieved. For example, stable extrachromosomal copy number can be increased by making the polycistronic cassettes part of an extrachromosomal replicon derived from, for example, bovine papilloma virus (BPV), human papovavirus (BK) or Epstein Barr virus (EBV) which maintain stable episomal plasmids at high copy numbers (e.g., with respect to BPV, up to 1000 per cell) relative to the 5–10 copies per cell achieved via conventional transfections. In this method the cassettes remain episomal, i.e., there is no selection for integration.

In this method, the BPV genome must be modified to allow replication in a human cell. This involves placing viral replicative functions under the control of strong, constitutive promoters. BK is a human papovavirus that is somewhat similar to SV40. It produces more stable episomal vectors, allowing for the achievement of high copy numbers which translate into higher expression of viral functions. Such high copy numbers can be directly selected using the tri-cistronic message cassettes.

High cassette copy numbers can also be achieved via gene amplification techniques. Such techniques include, but are not limited to, gene amplification driven by extrachromosomal replicons derived from, for example, BPV, BK, or EBV, as described above. Alternatively, the polycistronic, e.g., tricistronic, message cassettes can further comprise a gene amplification segment including, but not limited to, a DHFR or an ADA segment, which, when coupled with standard amplification techniques well known to those of skill in the art, can successfully amplify message cassette copy number.

The novel retroviral packaging cell lines of the invention can incorporate further modifications which optimize expression from retroviral LTR promoters. In one embodiment, the cell lines exhibit enforced expression of transcription factors that are known to activate retroviral LTR-driven expression in murine T cells. Such transcription factors include, but are not limited to, members of the ets family, cbf, GRE, NF1, C/EBP, LVa, LVb, and LVc. Retroviral packaging cell lines of this embodiment are designed to more efficiently produce, for example, murine leukemia virus-derived retroviral particles, including but not limited to, Moloney murine leukemia virus (MoMuLV)-derived retroviral particles.

Packaging cell lines with a capacity for increased transcription from the MuMoLv LTR can also be selected in a genetic screen which is executed as described in section 5.7, below. A representative selection scheme begins with a precursor cell line containing a quantifiable marker whose expression is linked to a MoMuLV LTR. Preferably, such an LTR/quantifiable marker construct is excisable. As such, the construct can further comprise an excision element which is equivalent to the proviral excision element described, above, in Section 5.1.

Precursor cells are infected with a cDNA library derived from murine T-cells. Cells with increased expression, as assayed by the expression of the quantifiable marker, are then identified. Recovery of the library DNA from such cells then identifies gene sequences responsible for such increased expression rates.

The resulting packaging cell lines produced via such a selection scheme exhibit an expression pattern of genes encoding retroviral regulatory factors which closely resembles a murine T-cell pattern of expression for such factors.

5.7 COMPLEMENTATION SCREENING METHODS

Mammalian cell complementation screening methods are described herein. Such methods can include, for example, a method for identification of a nucleic acid sequence whose expression complements a cellular phenotype, comprising: (a) infecting a mammalian cell exhibiting the cellular phenotype with a retrovirus particle derived from a cDNA or gDNA-containing retroviral vector of the invention, wherein, upon infection an integrated retroviral provirus is produced and the cDNA or gDNA sequence is expressed; and (b) analyzing the cell for the phenotype, so that suppression of the phenotype identifies a nucleic acid sequence which complements the cellular phenotype.

The term "suppression", as used herein, refers to a phenotype which is less pronounced in the presence in the cell expressing the cDNA or gDNA sequence relative to the phenotype exhibited by the cell in the absence of such expression. The suppression may be a quantitative or qualitative one, and will be apparent to those of skill in the art familiar with the specific phenotype of interest.

The present invention also includes methods for the isolation of nucleic acid molecules identified via the complementation screening methods of the invention. Such methods utilize the proviral excision and the proviral recovery elements described, e.g., in Section 5.1, above.

In one embodiment of such a method, the proviral excision element comprises a loxP recombination site present in two copies within the integrated provirus, and the proviral recovery element comprises a lacO site, present in the provirus between the two loxP sites. In this embodiment, the loxP sites are cleaved by a Cre recombinase enzyme, yielding an excised provirus which, upon excision, becomes circularized. The excised, circular provirus, which contains the lacO site is recovered from the complex mixture of recipient cell genomic nucleic acid by lac repressor affinity purification. Such an affinity purification is made possible by the fact that the lacO nucleic acid specifically binds to the lac repressor protein.

In an alternative embodiment, the excised provirus is amplified in order to increase its rescue efficiency. For example, the excised provirus can further comprise an SV40 origin of replication such that in vivo amplification of the excised provirus can be accomplished via delivery of large T antigen. The delivery can be made at the time of recombinase administration, for example.

In another alternative embodiment, the excised provirus may be recovered by use of a Cre recombinase. For example, the isolated DNA is fragmented to a controlled size. The provirus containing fragments are isolated via LacO/LacI. Following IPTG elution, circularization of the provirus can be accomplished by treatment with purified recombinase.

5.8 ANTISENSE METHODS

Antisense genetic suppressor element (GSE)-based methods for the functional inactivation of specific essential or non-essential mammalian genes are described herein. Such methods include methods for the identification and isolation of nucleic acid sequences which inhibit the function of a mammalian gene. The methods include ones which directly assess a gene's function, and, importantly, also include methods which do not rely on direct selection of a gene's function. These latter methods can successfully be utilized to identify sequences which affect gene function even in the absence of knowledge regarding such function, e.g., in instances where the phenotype of a loss-of-function mutation within the gene is unknown.

An inhibition of gene function, as referred to herein, refers to an inhibition of a gene's expression in the presence of a GSE, relative to the gene's expression in the absence of such a GSE. Preferably, the inhibition abolishes the gene's activity, but can be either a qualitative or a quantitative inhibition. While not wishing to be bound by a particular mechanism, it is thought that GSE inhibition occurs via an inhibition of translation of transcript produced by the gene of interest.

The nucleic acid sequences identified via such methods can be utilized to produce a functional knockout of the mammalian gene. A "functional knock-out", as used herein, refers to a situation in which the GSE acts to inhibit the function of the gene of interest, and can be used to refer to functional knockout cell or transgenic animal.

In one embodiment, a method for identifying a nucleic acid sequence which inhibits the function of a mammalian gene of interest can comprise, for example, (a) infecting a mammalian cell with a retrovirus derived from a GSE-producing retroviral vector containing a nucleic acid sequence from the gene of interest, wherein the cell expresses a fusion protein comprising an N-terminal portion derived from an amino acid sequence encoded by the gene and a C-terminal portion containing a selectable marker, preferably a quantifiable marker, and wherein an integrated retroviral provirus is produced that expresses the cDNA or gDNA sequence; (b) selecting for the selectable marker; and (c) assaying for the quantifiable or selectable marker, so that if the selectable marker is inhibited, a nucleic acid sequence which inhibits the function of the mammalian gene is identified.

In one preferred embodiment of this identification method, the fusion protein is encoded by a nucleic acid whose transcription is controlled by an inducible regulatory sequence so that expression of the fusion protein is conditional. In another preferred embodiment of the identification method, the mammalian cell is derived from a first mammalian species and the gene is derived from a second species, a different species as distantly related as is practical.

In a fusion protein-independent embodiment, the nucleic acid encoding the selectable marker can be inserted into the gene of interest at the site of the gene's initiation codon, so that the selectable marker is translated instead of the gene of interest. This embodiment is useful, for example, in instances in which a fusion protein may be deleterious to the cell in which it is to be expressed, or when a fusion protein cannot be made.

The method for identifying a nucleic acid sequence which inhibits the function of a mammalian gene, in this instance, comprises: (a) infecting a mammalian cell expressing a selectable marker in such a fashion with a retrovirus derived from a GSE-producing retroviral vector containing a nucleic acid sequence derived from the gene of interest, wherein, upon infection, an integrated provirus is formed and the nucleic acid sequence is expressed; (b) selecting for the selectable marker; and (c) assaying for the selectable marker, so that if the selectable marker is inhibited, a nucleic acid sequence which inhibits the function of the mammalian gene is identified. Selection for the marker should be quantitative, e.g., by FACS.

In an additional embodiment, the gene of interest and the selectable marker can be placed in operative association with each other within a bicistronic message cassette, separated by an internal ribosome entry site, whereby a single transcript is produced encoding, from 5' to 3', the gene product of interest and then the selectable marker. Preferably, the sequence within the bicistronic message derived from the gene of interest includes not only coding, but also 5' and 3' untranslated sequences.

The method for identifying a nucleic acid sequence which inhibits the function of a mammalian gene, in this instance, comprises: (a) infecting a mammalian cell expressing a selectable marker as part of such a bicistronic message with a retrovirus derived from a GSE-producing retroviral vector containing a nucleic acid sequence derived from the gene of interest, wherein, such infection, an integrated provirus is formed and the nucleic acid sequence is expressed; (b) selecting for the selectable marker; and (c) assaying for the selectable marker, so that if the selectable marker is inhibited, a nucleic acid sequence which inhibits the function of the mammalian gene is identified.

In an alternative embodiment, such a method can include a method for identifying a nucleic acid which influences a mammalian cellular function, and can comprise, for example, (a) infecting a cell exhibiting a phenotype dependent upon the function of interest with a retrovirus derived from a GSE-producing retroviral vector containing a test nucleic acid sequence, wherein, upon infection, an integrated provirus is formed and the test nucleic acid is expressed; and (b) assaying the infected cell for the phenotype, so that if the phenotype is suppressed, the test nucleic acid represents a nucleic acid which influences the mammalian cellular function. Such an assay is the same as a sense expression complementation screen except that the phenotype, in this case, is presented only upon loss of function.

The above methods are independent of the function of the gene of interest. The present invention also includes antisense methods for gene cloning which are based on function of the gene to be cloned. Such a method can include a method for identifying new nucleic acid sequences based upon the observation that loss of an unknown gene produces a particular phenotype, and can comprise, for example, (a) infecting a cell with a retrovirus derived from a GSE-producing retroviral vector containing a test nucleic acid sequence, wherein, upon infection, an integrated provirus is formed and the test nucleic acid is expressed; and (b) assaying the infected cell for a change in the phenotype, so that new nucleic acid sequences may be isolated based upon the observation that loss of an unknown gene produces a particular phenotype. Such an assay is the same as a sense expression complementation screen except that the phenotype, in this case, is presented only upon loss of function.

The present invention also includes novel methods for the construction of unidirectional, randomly primed cDNA libraries which can be utilized as part of the function-based methods described above. Such cDNA construction methods can comprise: (a) first strand cDNA synthesis comprising priming the first strand using a nuclease resistant oligonucleotide primer that encodes a restriction site; and (b) second strand cDNA synthesis comprising synthesizing the second strand an exonuclease deficient polymerase. The nuclease resistant oligonucleotide avoids the removal of a restriction site that marks orientation, thereby allowing for the construction of a unidirectional cDNA random primed cDNA library.

For example, a nuclease resistant chimeric oligonucleotide may be of the general structure: 5'-GCG GCG gga tcc gaa ttc nnn nnn nnn-3'. The modified backbone nucleotides are shown in upper-case, and is generally 4–6 bases, which is followed by one or two restriction sites comprised of normal DNA and nine degenerate nucleotides. A nuclease-deficient polymerase, such as the polymerase from bacteriophage phi-29, can be used.

The present invention also includes methods for the isolation of nucleic acid molecules identified via the antisense screening methods of the invention. Such methods utilize the proviral excision and the proviral recovery elements, as described, e.g., in Section 5.1, above.

In one embodiment of such a method, the proviral excision element comprises a loxP recombination site present in two copies within the integrated provirus, and the proviral recovery element comprises a lacO site, present in the provirus between the two loxP sites. In this embodiment, the loxP sites are cleaved by a Cre recombinase enzyme, yielding an excised provirus which, upon excision, becomes circularized. The excised, circular provirus, which contains the lacO site is recovered from the complex mixture of recipient cell genomic nucleic acid by lac repressor affinity purification. Such an affinity purification is made possible by the fact that the lacO nucleic acid specifically binds to the lac repressor protein.

In an alternative embodiment, the excised provirus is amplified in order to increase its rescue efficiency. For example, the excised provirus can further comprise an SV40 origin of replication such that in vivo amplification of the excised provirus can be accomplished via delivery of large T antigen. The delivery can be made at the time of recombinase administration, for example.

5.9 GENE TRAPPING METHODS

The present invention further relates to gene trapping-based methods for the identification and isolation of mammalian genes which are modulated in response to specific stimuli. These methods utilize retroviral particles of the invention to infect cells, which leads to the production of provirus sequences which are randomly integrated within the recipient mammalian cell genome. In instances in which the integration event occurs within a gene, the gene is "tagged" by the provirus reporter sequence, whose expression is controlled by the gene's regulatory sequences. By assaying reporter sequence expression, then, the expression of the gene itself can be monitored.

The gene trapping-based methods of the present invention have several key advantages, including, but not limited to, (1) the presence in the 3' LTR of a gene trapping cassette that is duplicated upon integration of the provirus into the host genome. This duplication results in the placement of the gene trapping cassette adjacent to genomic DNA such that polymerase entering the virus from an adjacent gene would transcribe the gene trapping cassette before encountering the polyadenylation signal that is present in the LTR. The inclusion of an IRES sequence in the gene trapping cassette allows the fusion between cellular and viral sequence to occur at any point within the mature mRNA, effectively increasing the number of possible integration sites that result in a functionally "tagged" transcript; and (2) the use of a quantifiable selectable marker that can be assessed by live sorting in the FACS, allowing for the isolation of clones that are induced, but also, of clones that tag genes that are repressed.

The term "modulation", as used herein, refers to an up- or down-regulation of gene expression in response to a specific stimulus in a cell. The modulation can be either a quantitative or a qualitative one.

Gene trapping methods of the invention can include, for example, a method which comprises: (a) infecting a mammalian cell with a retrovirus derived from a gene trapping vector of the invention, wherein, upon infection, an integrated provirus is formed; (b) subjecting the cell to the stimulus of interest; assaying the cell for the expression of the reporter sequence so that if the reporter sequence is expressed, it is integrated within, and thereby identifies, a gene that is expressed in the presence of the stimulus.

In instances wherein the gene is not expressed, or, alternatively, is expressed at a different level, in the absence of the stimulus, such a method identifies a gene which is expressed in response to a specific stimulus.

The present invention also includes methods for the isolation of nucleic acid sequence expressed in the presence of, or in response to, a specific stimulus. Such methods can comprise, for example, digesting the genomic nucleic of a cell which contains a provirus integrated into a gene which is expressed in the presence of, or in response to, the stimulus of interest; and recovering nucleic acid containing a sequence of the gene by utilizing the means for recovering nucleic acid sequences from a complex mixture of nucleic acid.

In one embodiment, the means for recovery is a lacO site, present in the integrated provirus. The digest fragment which contains the lacO site is recovered from the complex mixture of recipient cell genomic nucleic acid by lac repressor affinity purification. Such an affinity purification is made possible by the fact that the lacO nucleic acid specifically binds to the lac repressor protein.

Such methods serve to recover proviral nucleic acid sequence along with flanking genomic sequence (i.e., sequence contained within the gene of interest). The isolated sequence can be circularized, yielding a plasmid capable of replication in bacteria. This is made possible by the presence of a bacterial origin of replication and a bacterial selectable marker within the isolated sequence.

Upon isolation of flanking gene sequence, the sequence can be used in connection with standard cloning techniques to isolate nucleic acid sequences corresponding to the full length gene of interest.

5.10 EMBODIMENTS OF THE SCREENING ASSAY

As stated above, the methods of the present invention include methods for the identification and isolation of nucleic acid molecules based upon their ability to complement a mammalian cellular phenotype, antisense-based methods for the identification and isolation of nucleic acid sequences which inhibit the function of a mammalian gene, and gene trapping methods for the identification and isolation of mammalian genes which are modulated in response to specific stimuli. The compositions of the present invention include replication-deficient retroviral vectors, such as complementation screening retroviral vectors, antisense-genetic suppressor element (GSE) vectors, vectors displaying random peptide sequences, gene trapping vectors, libraries comprising such vectors, retroviral particles produced by such vectors and novel packaging cell lines. The following provides specific embodiments for the utilization of such methods, vectors and compositions for the elucidation of mammalian gene function.

5.10.1 BYPASS OF CONDITIONAL PHENOTYPES

Many phenotypes can be conferred upon mammalian cells in culture by conditional overexpression of known genes (e.g., growth arrest, differentiation). The interference with such phenotypes can be examined by overexpression of sense orientation genes or by functional knock-out (via GSE expression). Examples of this type of screening are given below.

A. Bypass of p53-mediated growth arrest and apoptosis.

Increases in the level of p53 can cause either growth arrest (generally by cell cycle arrest in G1) or programmed cell death. Cells lines that conditionally overexpressing p53 and contain a p53 functional knock-out will allow for the dissection of both of these processes. In the first case, mouse embryo fibroblasts (MEF) which lack endogenous p53 genes (from p53 knock-out mice) are engineered to conditionally express a fluorescently tagged p53 protein. When activated the fluorescent p53 is localized to the nucleus and enforces cell cycle arrest. Bypass of the arrest can be accomplished by overexpression of sense cDNAs or by expression of GSE fragments. Such a screen might identify components of the p53-degradative pathway, genes that do not affect p53 but allow cell cycle progression even in the presence of p53 and genes that affect p53 localization (p53 is not mutated but is mislocalized in a significant percentage of breast tumors and neuroblastomas). Therefore, use of a fluorescent p53 protein provides information as to the mechanism of bypass.

A very similar cell line can be used to dissect p53-mediated cell death. While p53 alone induces growth arrest in most fibroblasts, combination with certain oncogenes (myc, in particular) causes cell death. MEF cells that conditionally overexpress both myc and p53 are engineered. When activated in combination these genes induce cell death in a substantial fraction of cells. Rescue from this cell death via overexpression of sense oriented cDNAs can be used to identify anti-apoptotic genes (and possible p53-regulators as above). Rescue by GSE expression might identify components of the pathways by which myc and p53 induce cell death (downstream targets) or cellular genes that are required for the apoptotic program.

B. Bypass of the M1 component of cellular immortalization.

Immortalization of mammalian cells can be divided into two functional steps, M1 and M2. M1 (senescence) can be overcome in fibroblasts by viral oncoproteins that inactivate tumor suppressors, p53 and pRB. SV40 large T antigen is one such protein. Conditionally immortal cells have been derived using temperature sensitive or inducible versions of T-antigen. Upon T inactivation these cells senesce and cease proliferation. The growth of such cells may be rescued by introduction of sense and antisense libraries.

Similar screens can be undertaken with any gene that confers a phenotype upon overexpression. Essentially identical growth-rescue screens can also be undertaken using cytokines that induce growth arrest or apoptosis (e.g., TGF-beta in HMEC or Hep3B cells, respectively).

5.10.2 IDENTIFICATION OF CYTOKINES IN CIS AND TRANS.

Historically, several cytokines have been identified functionally by production in mammalian systems. Specifically, COS cells that express pools of transfected cDNAs have been used to prepare conditioned media that was then tested for the ability to induce growth of factor-sensitive cells. Growth regulatory cytokines may be identified (or survival factors that suppress cell death) by expression of cDNA libraries directly in the target cells. Such an approach has been hampered in the past by the low transfection efficiencies of the target cell types. For example, survival of hematopoietic stem cells is promoted by a variety of known and unknown factors. Therefore, upon infection of such cells with cDNA libraries derived from stromal cells that promote the growth and survival of stem cell populations, selection for surviving infected cells may identify those that carry cDNAs encoding necessary factors. Such factors would be produced in an autocrine mode. While this approach will identify trans-acting factors, cDNA that also act in cis (e.g., by short-circuiting growth-regulatory signal transduction pathways) will also be identified. These can be eliminated by searching for secreted growth regulatory factors using a two-cell system. In this case, one cell type is infected with a library and used as a factory to produce cDNA products, some of which will be secreted proteins. A second cell type that is factor-responsive is then plated over the cDNA expressing cells in a medium (e.g., soft-agar) that restricts diffusion. Responsive cells plated over the producing cells that elaborate the required factor will grow and the appearance of a colony of responsive cells will mark the underlying cells that elaborate the specific factor. The advantage of a two-cell system is more evident in the case where extracellular factors induce growth arrest or terminal differentiation. In such cases, expression in cis would be impractical since selection would be against the population expressing the desired gene. In trans, however, changes in recipient cells can be scored visually and the underlying expressing cells can be rescued for isolation of the desired gene. Similar two cell screens could be developed using the methods of the present invention to screen for factors that promote cell migration or cell-adhesion.

5.10.3 IDENTIFICATION OF SYNTHETIC PEPTIDES THAT CAN AFFECT CELLULAR PROCESSES

The present invention provides methods for the identification and isolation of peptides sequences by complementation type screens using vectors capable of displaying random synthetic peptide sequences that interact with a protein of interest in mammalian cells. Conventional screening methods of identifying proteins of interest have been conducted using phage systems and two hybrid screens in yeast. The present invention provides a novel screening method to extend this paradigm to mammalian cells.

A. Intracellular peptide display.

Thioredoxin may be utilized as a peptide delivery vehicle in the present screening method. Similar libraries of random peptide sequences can be expressed from retroviral vectors in mammalian cells. Expressed peptides that confer particular phenotypes can be isolated in genetic screens similar to those described above. The cellular targets of these peptides can then be isolated based upon peptide binding in vitro or in vivo.

B. Extracellular peptide display.

It is well established that the interaction between extracellular signaling molecules (e.g., growth factors) and their receptors occurred over large protein surfaces. The present invention provides a novel screen that allows for rapid identification of peptides in mammalian cells by expressing constrained peptides on the surface of receptor-bearing cells and selecting directly for biological function. A synthetic peptide can be displayed in a mammalian system by replacing one flexible loop of a synthetic peptide display vehicle or cassette, the minibody, with a polylinker into which a library of random oligonucleotides encoding random peptides may be inserted. The resulting synthetic chimera can be tethered to the membrane so that it appears on the cell surface by providing a heterologous membrane anchor such as that derived from the c. clegans decay accelerating factor (DAF). This chimeric protein could then serve as an extracellular peptide display vehicle. Peptide libraries in a retroviral vector could be screened directly for the ability to activate receptors, or screening in vivo could follow a pre-selection of a mini-library by phage display.

5.10.4 RESISTANCE TO PARASITE AND VIRAL INFECTION

Viruses and a number of parasitic organisms require intracellular environments for reproduction. The screens of the present invention may be utilized (e.g., sense overexpression, GSE expression, intracellular peptide display, extracellular peptide display) to identify routes to viral and parasite resistance.

For example, it has recently been demonstrated that resistance to HIV infection can be conferred by expression of a specific mutant gene. The methods of present invention may also be applied to develop a screen for other genes (natural, mutant or synthetic) that confer resistance to HIV infection or that interfere with the viral life cycle.

The methods of the present invention may also be applied to develop a screen for genes that interfere with the viral life cycle of an intracellular parasite, e.g., plasmodium.

5.10.5 IDENTIFICATION OF DRUG-SCREENING TARGETS FOR TUMOR CELLS THAT LACK SPECIFIC TUMOR SUPPRESSORS

A number of studies have identified two major tumor suppression pathways which are lost in a high percentage of human tumors. The p53 protein is functionally inactivated in approximately 50% of all tumors and the p16/Rb pathway is affected at an even higher frequency. Loss of these pathways for growth control is one of the most obvious distinctions between normal and tumor cells. Many chemotherapeutic drugs act by inducing cell death, and their selectivity is based upon the fact that tumor cells are proliferating while most of the normal cells in the body are quiescent. The methods of the present invention may also be applied to develop screens to identify gene products whose inactivation induces cell death specifically in cells lacking one or both of the two major tumor suppression pathways. This should provide drug screening targets that could lead to compounds that distinguish cells not based upon their proliferation index but based on their genotype.

Identification of such drug screening targets will depend upon that isolation of GSE sequences that can induce apoptosis specifically in the absence of p53 or in the absence of the p16/Rb pathway or both. Cells which conditionally lack either p53, p16/Rb or both can be prepared using conditional viral oncoproteins. For example, p53 can be conditionally inactivated using an inducible E6 protein or using a temperature sensitive T-antigen that has also lost the ability to bind Rb. Conditional loss of p16/Rb can be accomplished using conditionally expressed E7 or again with a ts-T antigen that is mutant for p53 binding. Such cells will be infected with a GSE library and passaged under conditions where p53 or p16/Rb regulation is intact. Those sequences that induce death in normal cells will be naturally counter-selected. The desired tumor suppression pathway will then be specifically inactivated and apoptotic cells will be purified by magnetic separation techniques that rely on the ability of annexing V to bind to the membrane of apoptotic cells. DNA prepared from apoptotic populations will then be used to rescue viral libraries. Several rounds of such screening should enrich for populations of GSE sequences that induce cell death in response to loss of tumor suppressor function.

5.10.6 IDENTIFICATION OF GENES INVOLVED IN METASTASIS (IN VIVO SELECTIONS)

The methods of the present invention may also be applied to develop screens to identify genes involved in metastasis. There are a number of well-characterized systems in which the ability of tumor cells to metastasize can be studied in vivo. The most common is the mouse footpad microinjection assay. Populations of non-metastatic cells can be infected with sense and antisense libraries. These can be injected into the mouse footpad and metastatic cells can be isolated after outgrowth of remote tumors. Rescue of viruses from such cells can be used to identify genes that regulate the ability of tumor cells to metastasize.

6. EXAMPLE

CONSTRUCTION OF THE RETROVIRAL MaRXII VECTOR

The following example provides the methods for the construction of replication-defective retrovirus, pMaRXII. The starting vector is pBABE puro (Morgenstern, 1990, Nucleic Acids Res. 18: 3587–3596), which is modified as follows:

The insertion of a synthetic linker comprising a loxP site was into the NheI site. The sequence of the linker containing the loxP site is as follows:

```
5'CTAGCATAACTTCGTATAATGTATGCTATACGAAGTTAT
   GTATTGAAGCATATTACATACGATATGCTTCAATAGATC3'
```

The insertion of this synthetic linker creates a loxP site while simultaneously destroying the 3' NheI site, leaving a unique NheI site.

The insertion of a polylinker between the BamHI and SalI sites of PBABE puro which contains a primer binding site for the universal (–20) sequencing primer and the lac operator sequence. The sequence of the upper strand of the polylinker is as follows:

```
5'GGATCCGTAAAACGACGGCCAGTTTAATTAAGAATTCGTTAACGCATGCCTCGAGTGTG
   GAATTGTGAGCGGATAACAATTTGTCGAC3'
```

The insertion of a PCR fragment comprised of the bacterial EM7 promoter and the zeocin resistance gene was amplified from pZEO SV (Invitrogen) such that the SalI and StuI sites were included at the 5' end of the fragment and the BspEI and ClaI sites were included at the 3' end of the fragment. The modified pBABE puro vector was digested with SalI and ClaI and ligated with the PCR fragment. The sequence of the upper strand of the PCR fragment is as follows:

```
5'gtcgacaggcctCGGACCTGCAGCACGTGTTGACAATTAATCATCGGCATAGTATATCG
   GCATAGTATAATACGACTCAC
   TATAGGAGGGCCACCATGGCCAAGTTGACCAGTGCCGTTCCGGTGCTCACCGCGCGCGACG
   TCGCCGGAGCGGTCGAGTT
   CTGGACCGACCGGCTCGGGTTCTCCCGGGACTTCGTGGAGGACGACTTCGCCGGTGTGGTC
```

-continued

```
CGGGACGACGTGACCCTGT

TCATCAGCGCGGTCCAGGACCAGGTGGTGCCGGACAACACCCTGGCCTGGGTGTGGGTGCG

CGGCCTGGACGAGCTGTAC

GCCGAGTGGTCGGAGGTCGTGTCCACGAACTTCCGGGACGCCTCCGGGCCGGCCATGACCG

AGATCGGCGAGCAGCCGTG

GGGGCGGGAGTTCGCCCTGCGCGACCCGGCCGGCAACTGCGTGCACTTCGTGGCCGAGGAG

CAGGACTGAttccggatttatcgat3'
```

The insertion of a PCR fragment comprised of the RK2 OriV which was amplified from the plasmid pMYC3 (Shah et al., 1995, J. Mol. Biol. 254: 608–622). The minimal oriV was chosen as defined in Shah et al. This PCR fragment contained a BspEI site at its 5' end and BglII and ClaI sites at its 3' end. The modified pBABE puro vector and the PCR fragment were both digested with BspEI and ClaI and ligated together. The sequence of the top strand of the PCR fragment is as follows:

```
5'TCCGGAcgagtttcccacagatgatgtggacaagcctggggataagtgccctgcggtat tgacacttgaggggcgcgact actgacagatgaggggcgcgatccttgacacttgaggggcagagtgatgacagatgagggg cgcacctattgacatttga ggggctgtccacaggcagaaaatccagcatttgcaagggtttccgcccgtttttcggccac cgctaacctgtcttttaac ctgcttttaaaccaatatttataaaccttgtttttaaccagggctgcgccctggcgcgtga ccgcgcacgccgaaggggg gtgccccccttctcgaaccctcccggAGATCTatcgat3'
```

The inclusion of a pUC origin of replication in an equivalent position to the RK2 OriV in either orientation was found to reduce both viral titer and expression levels in infected cells.

The F1 origin of replication was also inserted in the modified pBABE puro vector. The F1 origin of replication was amplified from pBluescript SK+ (Stratagene) and Not1 restriction sites were added to the 5' and 3' ends. This fragment was inserted into the modified vector following digestion of both the modified pBABE puro vector and the fragment with Not1. An orientation of the F1 origin was chosen that would yield, upon helper rescue, the sense strand of the cDNA. The sequence of the amplified F1 fragment is as follows:

```
5'gcggccgcGGGACGCGCCCTGTAGCGGCGCATTAAGCGCGGCGGGTGTGGTGGTTACGC

GCAGCGTGACCGCTACACTTG

CCAGCGCCCTAGCGCCCGCTCCTTTCGCTTTCTTCCCTTCCTTTCTCGCCACGTTCGCCGG

CTTTCCCCGTCAAGCTCTA

AATCGGGGGCTCCCTTTAGGGTTCCGATTTAGTGCTTTACGGCACCTCGACCCCAAAAAAC

TTGATTAGGGTGATGGTTC aCGTAGTGGGCCATCGCCCTGATAGACGGTTTTTCGCCCTTTGACGTTGGAGTCCACGTTC

TTTAATAGTGGACTCTTGT

TCCAAACTGGAACAACACTCAACCCTATCTCGGTCTATTCTTTTGATTTATAAGGGATTTT

GCCGATTTCGGCCTATTGG

TTAAAAAATGAGCTGATTTAACAAAAATTTAACGCGAATTTTAACAAAATATTAACGTTTA

CAAgcggccgc3'
```

The vector was further modified by the insertion of a PacI site between the BglII and ClaI sites of the modified pBABE puro vector using the following synthetic fragment

```
5'GATCTTTAATTAAAT3'
    AAATTAATTTAGC
```

The vector was still further modified by the insertion of a PmeI site into the BspEI of the modified pBABE puro vector site using the following synthetic fragment:

```
5'CCGGGTTTAAACT3'
    CAAATTTGAGGCC
```

The insertion of this fragment destroys one BspEI site, leaving the second site intact.

The vector was further modified by the insertion of a fragment comprising an IRES(EMCV)-Hygromycin resistance marker. The IRES hygromycin resistance cassette was created by amplification of the Hygromycin sequence from pBabe-Hygro (Morgenstern et al., 1990, Nucl. Acids Res. 18: 3587–3596) such that it lacked the first methionine of the hygromycin coding sequence and such that ClaI and SalI sites were added following the stop codon. This was inserted into the IRES-containing vector, pCITE (digested MscI-SalI) such that the first methionine of the hygromycin protein was donated by the vector. Methionine placement is critical for efficient function of the IRES. This cassette was amplified by PCR such that a SalI site was added upstream of the functional IRES and was re-inserted into the pBabe-Hygro following digestion of both with SalI and ClaI. This fragment was excised and inserted into the SalI site of the modified vector such that SalI sites were reformed on both sides.

The resulting vector is the MaRXII backbone (FIG. 1). The derivation of the specific purpose vectors from the MaRXII backbone is described below.

7. EXAMPLE

CONSTRUCTION OF THE RETROVIRAL VECTOR FOR SENSE COMPLEMENTATION SCREENING

This example provides the methods for constructing the sense-expression complementation screening vector, a pMaRXII derivative vector, pHygro MaRXII-LI (FIG. 3). The starting point for the construction of this vector begins with the MaRXII vector, as described above.

The vector is further modified by the insertion of a synthetic NotI linker which was ligated into the NheI site such that only one NheI site was left intact. The sequence of the NotI linker is as follows:

```
5'CTAGATGCGGCCGCTAG3'
    TACGCCGGCGATCGATC
```

A PCR fragment comprising the SV40 origin (below) was ligated into the PmeI site (in either orientation) to allow for replicative excision. The sequence of the fragment is as follows:

```
5'GGGGTTTAAACGACTAATTTTTTTATTTATGCAGAGGCCGAGGCCGCC
TCTGCCTCTGAGCTATTCCAGAAGTAGTGAGGAGGCTTTTTTGGAGGCCCC3'
```

The NsiI-NsiI fragment was deleted from pZero (Invitrogen) and this served as a template for the amplification of the lethal insert with primers that recognized the 5' end of the pTac promoter and the 3' end of the ccdB coding sequence. These primers added EcoRI and XhoI sites, respectively. The fragment was inserted following digestion of both the plasmid and the PCR product with EcoRI and XhoI.

This forms the basic sense expression vector. Other markers can replace the IRES-Hygromycin resistance cassette (e.g. IRES-Puromycin resistance, IRES-neomycin resistance, IRES-blasticidin resistance etc.). This vector has been used to produce virus population with titers exceeding $10^6$ particles/ml (as measured on NIH 3T3 cells). This is equivalent to titers obtained from the original pBabe vector. Thus, modifications have not compromised the ability of the vector to produce virus. Furthermore, expression levels obtained from the p.Hygro.MaRXII vectors approximate those obtained with other retroviral vectors (e.g. pBabe). This vector infects with high efficiency a wide variety of tissue culture cells including but not limited to: NIH-3T3, Mv1Lu, IMR-90, WI38, Hep3B, normal human mammary epithelial cells (primary culture), HT1080, HS578t. This vector has been used to test reversion/excision with the result that following infection with a Cre-encoding virus, >99% of cells lose the phenotype conferred by the MaRX II provirus. Following recovery protocols detailed below, >1×10³ independent colonies can be routinely recovered from 100 μg of genomic DNA containing the provirus (without T-antigen driven amplification).

8. EXAMPLE

CONSTRUCTION OF THE RETROVIRAL VECTOR FOR ANTISENSE COMPLEMENTATION SCREENING

This example provides the methods for constructing the antisense screening vectors, the MaRXIIg series, a pMaRXII derivative vector.

Construction of the MaRXIIg series began with a MaRXII vector as described above, except that it lacked the PacI site. A marker, in most cases hygromycin-resistance, is inserted into the unique SalI site created.

MaRXIIg

The pMARXII vector was modified by the following steps:

A synthetic polylinker of the following sequence was added between the BamHI and SalI sites of MaRXII.

```
5'-GATCGTTAATTAACAATTGG-3'
3'-   CAATTAATTGTTAACCAGCT-5'
```

A synthetic NotI linker of the following sequence was ligated into the NheI site such that only one NheI site was left intact.

```
5'CTAGATGCGGCCGCTAG3'
   TACGCCGGCGATCGATC
```

The CMV promoter was inserted into the modified pMARXII vectors as follows. The CMV promoter sequence was amplified from pcDNA3 (Invitrogen) and this served as a template for amplification of the lethal insert with primers using the following oligonucleotides:

```
5'-GGG AGA TCT ACG GTA AAT GGC CCG CC-3'

5'-CCC ATC GAT TTA AAT AAG TTT AAA CGG GCC CTC TAG GCT
CGA G-3'
```

The amplification product was digested with BglII and ClaI and inserted into a similarly digested MaRXII derivative. The polylinker was then altered by the insertion of the EcoRI-XhoI fragment of the MaRXII polylinker between the EcoRI and XhoI sites of the modified vector. This formed the MaRXIIg vector where the CMV promoter drives GSE expression using the 3' LTR polyadenylation signal to terminate the transcript (FIG. 7).

MaRXIIg-dccmv

The MaRXII derivative from above was digested with NheI. A CMV promoter fragment was prepared by amplification of pHM.3-CMV with the following oligonucleotides:

```
5'-GGG GCT AGC ACG GTA AAT GGC CCG CC-3'

5'-CCC TCT AGA TTA ATT AAG TTT AAA CGG GCC CTC TAG GCT
CGA G-3'
```

The CMV fragment was digested with NheI and XbaI and ligated to the MaRXII derivative. An orientation was chosen such that transcription proceeded in the same direction as does transcription from the LTR promoter (FIG. 8).

MaRXIIg-VA

The MaRXII derivative from above (MaRXIIg section) was digested with NheI. An adenovirus VA RNA cassette was prepared by amplification of a modified VA RNA gene (see Gunnery, 1995 Mol Cell Biol 15, 3597–3607 (1995)) with the following oligonucleotides:

```
A. GGG GCT AGC CTA GGA CCG TGC AAA ATG AGA GCC-3'

B. 5'-GGG TCT AGA TTA ATT AAG TTT AAA CGG CCA AAA AAG
CTT GCG C-3'
```

This fragment was digested with NheI and XbaI and ligated into the digested MaRX II derivative. An orientation was chosen such that transcription proceeded in the same direction as does transcription from the LTR promoter (FIG. 9).

All three types of antisense vectors have been used to generate high-titer retroviruses which perform equivalently to p.hygro.MaRXII.

9. EXAMPLE

CONSTRUCTION OF THE RETROVIRAL VECTOR FOR GENE TRAPPING

This example provides the methods for the construction of the gene trapping vectors—pTRAP II, a pMaRXII derivative vector (FIG. 6).

The pTRAPII vectors are prepared in a MaRXII backbone, as described above.

The pMaRXII vector was modified by the following steps:

A synthetic polylinker was added between the BamHI and SalI sites of MaRXII, of the following sequence:

```
5'-GATCGTTAATTAACAATTGG-3'
3'-    CAATTAATTGTTAACCAGCT-5'
```

A second synthetic polylinker was added between the BglII and ClaI sites. The top strand of this linker is as follows:

```
5'agatctTGTGGAATTGTGAGCGGATAACAATTTGGATCCGTAAAACGACGGCCAGTTTA

ATTAAGAATTCGTTAACGCATGCCTCGAGGTCGACatcgat3'
```

This incorporates restriction sites for excision from the genome as well as sequencing primer binding sites and the lacO recovery element.

The 3' LTR and accompanying sequences were removed from the pBabe-Puro using ClaI and NotI. These were inserted into a ClaI and NotI digested pBluescript SK+. Site directed mutagenesis was used to delete a segment of the 3' LTR. This was accompanied by a small insertion. The sequences that surround and thus define the deletion are as follows:

```
5'-TAACTGAGAA TAGAGAAGTT CAGATCAAGG TCAGGAGATC CCTGAGCCCA

CAACCCCTCA CTCGGGGCGC-3'
```

This fragment was re-inserted into ClaI-NotI digested pBabe-puro to create pBabe-puroSIN. This plasmid was the source for the self-inactivating LTR that was inserted into the gene trapping vector using the unique NheI and SapI restriction sites.

The plasmid pPNT (see Brugarolas et al., 1995) was modified by replacement of the neomycin coding sequence with that of hygromycin (from pBabe-Hygro). This created a hygromycin resistance gene flanked by the PGK promoter and the PGK polyadenylation signals. This cassette was amplified by PCR and inserted into the ClaI site of the gene trapping vector such that transcription from the PGK promoter opposed transcription from the 5' LTR.

A gene trapping cassette was inserted in the NheI site in the 3' LTR. This gene trapping cassette consists of a quantifiable marker whose expression is promoted by an IRES sequence. In most cases the IRES sequence is derived from EMCV although IRES sequences from other sources are equally suitable. Thus far, IRES linked beta-galactosidase and IRES linked green fluorescent protein markers have been incorporated.

10. EXAMPLE

CONSTRUCTION OF THE RETROVIRAL VECTOR FOR MULTIPLE ORGANISM DISPLAY VECTORS

This example provides the methods for constructing the Multiple Organism Display or peptide display vectors—pMODisI and pMODisII, pMaRXII derivative vectors (FIGS. 4 and 5).

The pMODis vectors are designed to act as dual purpose vectors that allow the combination of phage display approaches with functional screening in mammalian systems. These are designed to allow the display of random peptide segments on the surface of filamentous bacteriophage. The displayed peptides can be screened via an affinity approach with a known ligand or a complex mixture of ligands (e.g. fixed cells). The pool of phages which bind to the desired substrate can then be used to generate retroviruses that can be used to infect mammalian cells. A large pool of phage can then be tested individually for the ability to elicit a phenotype. pMODisI is designed to allow display on the surface of phage and of mammalian cells. Additionally by passage through a specific host strain pMODisI can be used to direct secretion of displayed peptides from mammalian cells. pMODisII is an intracellular display vector. Both are created by the insertion of cassettes between the EcoRI and XhoI sites (destroying these sites) of p.Hygro.MaRXII. The design of the individual cassettes is as follows.

pMODisI cassette

The pMODisI cassette contains the following elements in order 1. the beta-globin minimal splice donor site
2. the pTAC promoter
3. a synthetic ribosome binding site
4. the pelB secretion signal
5. the beta globin minimal splice acceptor site
6. a mammalian secretion signal (e.g. from the V-J2-C region of the mouse Ig kappa-chain)
7. the minibody 61 residue peptide display vehicle sequence (Tramontano, J. Mol. Recognit. 7: 9–24 (1994))
8. an FRT recombinase site
9. the 37 amino acid DAF-1 GPI anchor (see Rice et al., PNAS 89: 5467–5471 (1992))
10. an FRT recombinase site
11. an amber stop codon
12. the C-terminus of the geneIII protein, amino acids 198–406
13. non-amber stop codons In an amber suppressor strain and in the presence of helper phage, a geneIII fusion protein is produced and displayed on the surface of the M13-type phage. This allows display of random peptide sequence cloned into one or both of the two constrained loops of the minibody to be displayed on the phage surface. Expression in packaging cells of MODisI genomic retroviral RNA allows removal of the bacterial promoter and secretion sequences by pre-mRNA splicing and causes translation in the mammalian cell to begin at the first methionine of the minibody sequence. Furthermore, in a mammalian cell, the amber codon would terminate translation prior to the geneIII sequence creating a membrane-bound extracellular minibody that displays a random peptide sequence. The minibody could be converted to a secreted protein by passage through a FLP-expressing strain of bacteria. This would cause site-specific recombination at the FRT sites and deletion of the membrane anchor sequence.

pMODisII cassette

The pMODisII contains the following elements in order.

1. the beta-globin minimal splice donor site
2. the pTAC promoter
3. a synthetic ribosome binding site
4. the pelB secretion signal
5. the beta globin minimal splice acceptor site 7. the thioredoxin peptide display vehicle sequence (Colas et al., Nature 380: 548–550 (1996))

11. an amber stop codon 12. the c-terminus of the geneIII protein, amino acids 198–406

13. non-amber stop codons

This vector is designed for intracellular peptide display. As with pMODis1, the bacterial promoter and signal sequences are removed upon retrovirus production by pre-mRNA splicing.

Both of the pMODis vectors can also be used directly for peptide display in mammalian systems.

11. EXAMPLE

PREPARATION OF LIBRARIES

The following example provides the methods for the construction of the libraries of the present invention.

11.1 CONSTRUCTION OF SENSE EXPRESSION LIBRARIES IN p.Hygro.MaRX II-LI

Preparation of the library vector as follows.

For preparation of the library vector, 10–20 µg of twice CsCl purified vector are digested with 5U/µg of EcoR1 and XhoI for 90 min at 37° C. This digestion is directly loaded onto a 1% agarose gel (SeaKem GTG), and cut vector is separated by electrophoresis in TAE buffer. The vector band is excised following visualization by long-wave UV light. The cut vector is eluted from the agarose by electrophoresis in dialysis tubing. The vector is further purified by phenol/chloroform extraction and ethanol precipitation. It is expected that a vector which is suitable for library preparation can generate >5×10$^6$/0.5 µg colonies with <10% background (insert-less) upon ligation with an EcoRI/XhoI digested test insert.

Preparation of cDNA libraries cDNA synthesis begins with an RNA population that is >10–20 fold enriched (as compared to total RNA) for mRNA. First strand cDNA synthesis is accomplished by standard protocols using SuperscriptII reverse transcriptase. 5-me-dCTP replaces dCTP in the first strand synthesis reaction to block digestion of the newly-synthesized cDNA with XhoI. The first strand cDNA primer is as follows:

5'-GAG AGA GAG AGT CTC GAG TTT TTT TTT TTT TTT TTT-3'

The first nine nucleotides are modified backbone (phosphorthioate) to prevent nuclease degradation of the XhoI site (CTCGAG). Other modifications to the backbone (e.g., p-ethoxy, Peptide-nucleic acid—PNA) would also serve. Synthesis is initiated by addition of reverse transcriptase in the presence of a saturating amount of the primer and following a controlled hybridization at 37° C. to prevent synthesis of long oligo dT tails.

Second strand synthesis is accomplished by E. Coli DNA polymerase I in the presence of RNAse H and E. Coli DNA ligase. Termini generated by second strand synthesis are made blunt by the action of T4 DNA polymerase.

Double stranded cDNAs are size fractionated by gel filtration chromatography on Biogel A50M as described by Soares (Soares et al., 1994, Proc. Natl. Acad. Sci. 91:9228–9232).

Size fractionated cDNAs are ligated to commercial EcoRI adapters (Stratagene), and then treated with XhoI to create cDNA fragments with EcoR1 (5') and XhoI (3') ends. Unligated adapters are removed by chromatography on Sepharose CL4B (Pharmacia). The adapter-bearing cDNA is phosphorylated using polynucleotide kinase and is ligated using T4 DNA ligase to the EcoRI-XhoI digested library vector at 16° C. for up to two days (600 ng. vector plus 250 ng insert in a volume of 10–20 µl). The library is amplified by electroporation into ElectroMax DH12S (Gibco-BRL) which are plated on 100 150 mm LB+ampicillin+IPTG plates. Alternatively, the library may be amplified in liquid media containing ampicillin and IPTG (to select against non-recombinant clones). At a minimum a library of >5×10$^6$ clones is required. This is routinely achieved using our protocols.

Normalization of cDNA libraries

We use two protocols for the normalization of cDNA libraries. Both are based upon those reported by Soares et al., 1994. This precise procedure has been used, but we have also developed a modified and streamlined using biotinylated oligonucleotides to reduce the number of steps.

Rescue of single stranded DNA

The retroviral library in E. coli DH12S is grown in 100 ml of culture volume to mid-log phase and is then infected at a m.o.i of 10 with a helper phage (e.g. M13K07 or VCS-M13+). The culture is incubated for from 2 two 4 hours at 37° C. after which single stranded DNA is purified from the supernatant using standard protocols.

Purification of the single stranded library DNA

The DNA prepared as described above is a mixture containing single stranded library DNA, ssDNA from the helper phage and double stranded DNA from lysed bacteria in the culture. The DNA mixture is first digested with XbaI that cuts only double-stranded DNA within the retroviral LTR. This mixture is then treated with Klenow DNA polymerase in the presence of dATP, dGTP, dCTP and Bio-16-dUTP. This treatment will incorporate a biotin residue on both ends of each fragment. The DNA population is then annealed to an excess of a 40-mer oligonucleotide that is complementary to the helper phage. This oligonucleotide carries a biotin residue at its 5' terminus (C16-biotin, Peninsula Labs). The unincorporated nucleotides and single stranded, biotinylated oligonucleotides are removed by chromatography on sepharose CL-4B. The biotinylated DNA fragments and the oligo-bound helper phage DNA is removed from the population by incubation with magnetic-streptavidin beads (Dynal). This yields a cDNA population that is comprised essentially of the single stranded library.

Normalization of the library

Normalization of the cDNA library is accomplished by reassociation kinetics (C0t). The purified single stranded DNA is first annealed to a common primer. In our protocol this is a biotinylated oligo dT$_{18}$ primer while in the Soares protocol the primer is not biotinylated. This primer is extended by Klenow polymerase in the presence of a mixture of dNTPs and di-deoxyNTPs to synthesize fragments (average ~200 nt. in size) complementary to the 3' end of our cDNA population. Again unincorporated primers and nucleotides are removed by chromatography on CL4B. The purified DNA is concentrated by ethanol precipitation.

For the reassociation kinetics reaction, 100–200 ng. of purified, partly duplex DNA is resuspended in 2.5 µl of formamide and heated at 80° C. for several minutes. An excess (~5 µg) of oligo dT25 is added to block interaction of the extension products (see above) with single stranded library though the oligo dT stretches that are present at the end of each clone. 0.5 µl of 0.5M NaCl is added along with 0.5 µl of 100 mM Tris-HCl, 100 mM EDTA, pH 8.0 and 0.5 µl water. The mixture is incubated at 42° C. for 12–24 hours to produce a C0t of 5–20.

Re-annealed duplexes represent abundant clones which are removed from the mixture (following dilution in binding buffer) by incubation with magnetic streptavidin beads. The non-bound fraction represents the normalized library and is enriched for unique sequences. This single stranded library is concentrated by precipitation and is annealed to an excess of a vector primer that lies downstream of the XhoI cloning site (lacO primer). Extension of this primer with T4 DNA polymerase (or the like) creates partially double stranded circles which are used to transform electrocompetent DH12S bacteria to produce the normalized library.

The transformed population is used for preparation of high-quality DNA by standard protocols.

Selection of retroviral sub-libraries specific to a given location within a genome Sublibraries that contain sequences derived from specific loci in a given genome can be selected from the single-stranded DNA prepared as above. Loci-specific DNA sequences that contain mapped, yet unknown genes can be obtained as sorted chromosomes or as fragments born on YAC or BAC vectors. These sequences are obtained in pure form or are purified by standard methods. Purified DNA is digested with a restriction enzyme with a four-based recognition sequence. A double stranded oligonucleotide is ligated to the ends of these fragments. Excess double stranded oligonucleotide is removed by column chromatography and the fragments are amplified by PCR with a biotinylated primer that corresponds to one strand of the double stranded oligonucleotide. This results in the production of a population of biotinylated DNA fragments that are derived from a specific genomic locus. This population is then annealed in the presence of appropriate competitive DNA sequences (e.g., yeast genomic DNA, highly repetitive human DNA) to single-stranded retroviral cDNA libraries prepared as above. cDNAs that are derived from the region of interest can then be purified using magnetic streptavidin beads and rescued in bacteria as described above. The resulting retroviral sub-library is greatly enriched for sequences that are contained on the original sorted chromosome, YAC, or BAC. The ability of sequences in this sub-library to give rise to a known phenotype can then be tested following packaging and infection of the appropriate cell type.

11.2 PREPARATION OF UNIDIRECTIONAL ANTISENSE LIBRARIES

Unidirectional antisense libraries are prepared essentially as described for the sense orientation libraries (see above). Exceptions are as follows:

First strand synthesis is accomplished using a modified backbone random primer that incorporates a restriction site. For our purposes we use the oligonucleotide:

5'-GCG GCG gga tcc gaa ttc nnn nnn nnn-3'

As with sense orientation libraries, the first six nucleotides contain a modified backbone structure that makes them nuclease resistant.

Following second strand synthesis, the library DNA is blunt-ended and ligated to XhoI linkers. These have the following structure

5'-TCTCTAGCTCGAGCAGTCAGTCAGGATG-3'

3'-ATAAGAGATCGAGCTCGTCAGTCAGTCCTAC-3'

Ligation of these linkers permits amplification of the library by PCR. In this case, the purified cDNA must be digested with both EcoRI and XhoI. Alternatively, commercially available XhoI adapters are ligated to the cDNA. In this case, the library cannot be amplified by PCR, and digestion of the linker-ligated cDNA is with EcoRI. Size selection of the cDNAs is accomplished by gel electrophoresis since the goal is to isolate fragments with an average size of 200–500 nucleotides. This isolated DNA is then ligated into the MaRXIIg (or IIg-VA or IIg-dccmv) ad described above. Normalization is also accomplished as described for the sense expression libraries except that the primer used for extension of the library circles is derived from a combination of the vector (lacO site) and the polylinker since these clones have no oligo dT sequences. This also necessitated the addition during the re-annealing (C0t) step of an excess of the non-biotinylated primer to suppress hybridization via primer sequences.

11.3 SINGLE GENE UNIDIRECTIONAL ANTISENSE LIBRARIES

Single-gene antisense libraries (for use in targeted functional knockouts) are prepared essentially as described above except that the template for first strand synthesis is a transcript produced from a cloned cDNA using a bacteriophage RNA polymerase (typically T3, T7 or SP6 polymerase). The second deviation is that is type of library is not normalized.

12. EXAMPLE

PREPARATION OF VIRUS AND INFECTION AND RECOVERY

The following example provides the necessary protocols for the preparation of the virus and infection of cells with the virus, in addition to recovery of the provirus.

12.1 TRANSFECTION OF PACKAGING CELLS AND INFECTION WITH VIRUS

1. Plate $6 \times 10^6$ packaging cells/10 cm plate. 37 c for O/N. Cells should be about 70–80% confluent.
2. Replace medium (10 ml). 37 C for 1–4 hours.
3. Prepare 2 ml of DNA ppt solution for each transfection in two eppendorf tubes.
   ug DNA+X ul water=450 ul total volume add 50 ul 2.5 M $CaCl_2$/0.01 M HEPES (pH5.5). Mix dropwisely add 500 ul 2×BBS (50mM BES, 280mM NaCl, 1.5 mM $Na_2HPO_4$, pH 6.95) to DNA/$CaCl_2$ mix while gently bubbling in DNA/$CaCl_2$ mix with a pasture pipette immediately and dropwisely add DNA ppt solution to cells while gently swirling the plate (2 ml DNA ppt solution/10 cm plate)
4. 37° C. for O/N.
5. Replace medium. (Option: at this step dexoamethasone and sodium butyrate can be added to medium at final concentrations of 1 $\mu$M and 500 $\mu$M, respectively. This increases the viral titer by 2–10 fold)
6. 32° C. incubation for 48 hours.
7. Collect virus supernatant and filter it through a 0.45 uM syringe filter unit. (Optionally, packaging cells can be eliminated by spinning the virus supernatant at 1K for 5 minutes.)
8. Dilute virus supernatant in fresh growth medium and add polybrene to a final concentration of 8 ug/ml. Add the mixture to cells.
9. Spin the plates at 1.8K for I hour at RT.
10. 32° C. incubation for O/N.

At this point, multiple infection cycles can be done by replacing the media on the producer cells and repeating steps 7–10 at 6 hour intervals.

11. Replace medium. 37° C. incubation.
12. Cells are analyzed or drug selection applied after 2 days.

12.2 PROVIRAL EXCISION AND RECOVERY

12.2.1 STRUCTURE OF THE Cre AND CreT VIRUSES

Excision of viral plasmids for reversion of phenotypes is accomplished using a virus which directs the expression of Cre recombinase from the LTR promoter. This virus was prepared by excision of the Cre sequence from pMM23 (see Qin et al., 1994, PNAS 91: 1706–1710) and insertion of that fragment into pBabe-Puro. Derivatives with other markers have also been constructed. For replicative excision, a cassette that consists of the coding sequence of large T antigen (from pAT.-t (a T antigen clone that can encode large T but not small t) fused to the IRES sequence from EMCV (derived from pCITE) was inserted downstream of the Cre sequence.

12.2.2 EXCISION IN VIVO

Infect (as described above) MaRX virus-containing cells with pBABE-puro-Cre virus when cells are at 40–80% confluence in 10 cm using 8 ml virus (generated as described above)+2 ml medium+10 $\mu$l 8 mg/ml polybrene For reversion, the cells are maintained at 32° C. overnight and then transferred to 37° C. These cells are then selected for the presence of the Cre virus by incubation in selective media (e.g. containing puromycin). After one or two passages, the cells may be analyzed for loss of the phenotype.

For in vivo excision for recovery of the viral plasmid, cells are infected with either the Cre or the Cre-T virus and then incubated overnight at 32° C. Cells are subsequently transferred to 37° C. for an additional 6–24 hours. DNA is prepared and the proviral plasmid is recovered by one of the methods described below.

12.2.3 PREPARATION OF DNA FOR AFFINITY RECOVERY

For recovery of provirus by affinity purificatior, a 10 cm dish at confluence is lysed as described below. For provirus that has been excised in vivo, cells will have been treated as described above. For recovery of provirus following purification, infected cells at 80–100% confluence are used.

lysis buffer in 10 mM Tris, pH 8.0, 150 mM NaCl 10 mM EDTA, 1% SDS, 500 $\mu$g/ml prot K, 120 $\mu$g/ml RNese A.

1. lyse cells in 10 ml of lysis buffer/10 cm dish
2. incubate at 55° C. for 3 hours
3. add an equal volume of phenol/chloroform, rotate 10 minutes, spin
4. add ⅕ vol 8M Kac and 1 vol chloroform, rotate 10 minutes, spin
5. add 2 volumes of ethanol and spool onto a glass rod
6. Wash genomic 3X in 70% ethanol
7. AIR dry pellet and resuspend in TE

12.2.4 PREPARATION OF LacI AFFINITY BEADS

LacI beads for affinity purification are prepared in one of two ways. A procedure has been published for the preparation of magnetic beads bearing a lacI-Protein A fusion. These have been prepared exactly as described by Lundeberg et al. Genet. Anal. Tech. Appl 7: 47–52 (1990).

12.2.5 RECOVERY OF DNA ON lacI BEADS

Proviral DNA can be recovered on LacI beads prepared as described above. For recovery of provirus that is excised in vivo or for recovery of provirus for excision in vitro, DNA preparations must be slightly sheared to reduce viscosity. This can be accomplished by brief sonication, repeated passage though a narrow gauge needle or by nebulization.

1. 1–50 $\mu$g of DNA is diluted to 58 $\mu$l ddH2O
2. add 15 $\mu$l of 5X binding buffer
3. pellet 60 $\mu$l lacI beads on magnetic concentrator
4. remove the supernatant and resuspend in DNA solution
5. rotate at 37° C. for 60 minutes
6. Pellet beads and wash 1X with 250 $\mu$l 1X binding buffer
7. Resuspend in 75 $\mu$l IPTG elution buffer plus 5 $\mu$l 25 mg/ml IPTG
8. rotate at 37° C. for 30 minutes
9. Add 30 $\mu$g of glycogen and ethanol precipitate For provirus that has been excised in vivo, electroporate the recovered DNA into DH12S/trfA.

For excision/recircularization in vitro:

Excision/recircularization in vitro is accomplished in one of several ways. The DNA can be treated with commercially available Cre recombinase according to the manufactures instructions. The recircularized plasmids can then be used to transform E. coli by electroporation. Alternatively, most of the MaRX derived vectors have unique rare-cutting restriction enzyme sites adjacent to the loxP sites. These enzymes (e.g. NotI in p.Hygro.MaRX II) can be used for digestion of the proviral DNA followed by recircularization using T4 DNA ligase to create a plasmid that can be both propagated in bacteria and used for the production of subsequent generations of retroviruses.

Alternative recovery method: Hirt extraction

Following in vivo excision, proviral plasmids can be recovered by the Hirt procedure (Hirt, B., J. Mol. Biol. 26: 365–369 (1967)). This can be used for the recovery of single clones but it is relatively inefficient and thus cannot be used for high-efficiency recovery of enriched sub-libraries.

1. Following in vivo excision, wash cells twice with 10 ml of PBS.
2. Add 3 ml of 0.6% SDS/10 mM EDTA (pH7.5)/10 cm plate. Incubate at RT for 15 minutes to lyse cells.
3. Transfer lysate to a 15 ml tube with a scraper and a blue tip cut wide at end (to avoid shearing genomic DNA).
4. Add 750 ul of 5 M NaCl. Mix by gently inverting the tube.
5. Incubate at 4° C. for more than 8 hours.
6. Spin at 15K for 20 minutes in JA20 at 4° C. and save supernatant.
7. Extract with 1 vol of phenol/chloroform and then with chloroform.
8. ppt DNA by adding 20 ug of glycogen and 2.5 vol of EtOH.
9. Dissolve DNA in 200 ul of water. Extract with 1 vol. of phenol/chloroform and then with chloroform.
10. Dissolve DNA in 10 ul of water.
11. Electroporate DNA into DH12S/trfA (see below).
    5 ul of recovered DNA+50 ul of cells on ice
    1.8 kV×25 uFD×200 Ω in 0.1 cm cuvette (BioRAD)
    add 1 ml of 2XYT
    37° C. recover for 1 hour
    Plate 200 ul on LB(½ NaCl, pH7.5)-zeocine (25 ug/ml)
    37° C. for O/N This procedure generally yields several hundred proviral colonies.

12.2.6 PROVIRAL HOST STRAIN: DH12S/trfA

The RK2 replication origin (oriV) requires a replication protein, trfA for function. Otherwise it is a silent DNA element thus allowing it to co-exist with a pUC replication origin on the same plasmid. The excised provirus depends on the RK2 origin for replication and thus for propagation of this plasmid, trfA must be provided in trans. Thus, a trfA-helper strain has been constructed using DH12S as a founder strain. Several characteristics of DH12S prompted its choice for construction of the helper strain. Firstly, it is defective in the restriction system that causes degradation of methylated DNA. Secondly, it is recA, recBC and will thus more stably maintain plasmids. Thirdly, it can be used for the production of single-stranded DNA. Finally, DH12S can give rise to high-efficiency electrocompetent cells.

Since oriV-based plasmids are generally maintained at low copy number, a copy-up mutant of the replication protein (trfA-267 L; Blasina, 1996. Copy-up mutants of the plasmid RK2 replication initiation protein are defective in coupling RK2 replication origins. Proc. Natl. Acad. Sci. U.S.A. 93: 3559–3564 (1996)) was used for the preparation of the strain. This mutant was first cloned into pJEH118 (Fabry et al., 1988, FEBS Letters 237: 213–217) to place it under the control of the pTac promoter. This allows inducible, high level expression which helps to offset the loss in expression levels that occur as trfA integrated into the chromosome at single. A kanamycin resistance marker was then cloned downstream of the trfA cassette. The entire cassette was excised and inserted into a lambda phage vector (lambda-NM540) which was packaged in vitro and used for the preparation of a DH12S lysogen. Several lysogens were tested for the ability to propagate oriV plasmids and one was chosen as DH12S/trfA.

13. PRODUCTION OF PACKAGING CELL LINES

13.1 CREATION OF CASSETTES THAT PROVIDE VIRAL FUNCTIONS

Three viral functions are provided in trans by packaging cell lines. These are gag, pol and env. In general, either all three are provided by a single cassette or the gag/pol and env functions are separated onto two cassettes. To create directly selectable cassettes that can provide viral functions in trans, genes encoding viral proteins have been transferred from a helper plasmid that consists of a defective provirus (psi-e; Mann et al., Cell 33: 153–9 (1983)) to pBluescript in two formats.

13.2 SINGLE GENE HELPER CASSETTES

To produce an ecotropic single gene helper cassette, the XhoI-ClaI fragment was purified from psi-e and transferred to a similarly digested pBS-SK+to create pBS+psixc. The end of the envelope gene was reformed by adding a ~100 nt PCR product which spanned the sequences from the ClaI site to the stop codon of the envelope protein. This procedure also added a unique EcoRI site to the 3' end of the helper cassette. The PCR product was inserted into pBS-psiXC following digestion of both DNAs with EcoRI and ClaI. The resultant plasmid was pBS-psi-XE. The 5' end of the helper cassette was created by insertion of a PCR product which spanned from the retroviral splice donor site at the 5' end of the packaging signal to the unique XhoI site of MoMuLv.

This PCR product was inserted into an XhoI digested pBS-psiXE in such a way that a unique SspI site was present at the 5' end of the cassette. This formed pBS-psiCOMP. This helper cassette could encode gag, pol and env, but lacked the LTR elements and tRNA primer binding sequences necessary to produce a replication competent virus. To allow direct selections for viral functions, a tri-cistronic message cassette was created by inserting two tandem IRES-linked markers downstream from the end of the envelope sequence. In this case the cassette contained an EMCV IRES linked to human CD8 protein (a cell surface marker) linked to another EMCV IRES linked to the hygromycin resistance gene. This was inserted from EcoRI to NotI in pBS-psiCOMP to form pBS-psiCD8H. The cassette from this plasmid can be inserted into any expression vehicle following excision by SspI and NotI.

Separation of helper functions onto two cassettes was accomplished by creating deletions of pBS-psiCOMP. The env function was isolated by digestion of pBS-psiXE with XhoI and XbaI followed by insertion of a linker sequence that reformed both restriction sites. Removal of env from pBS-psiCOMP was accomplished by digestion with HpaI and EcoRI followed by ligation with a synthetic fragment that repaired the 3' end of pol and that reformed both the HpaI and EcoRI restriction sites. The single cassette amphotropic envelope (Ott, D. E. et al., J. Virol. 64, 757–766 (1990)) was formed by PCR followed by insertion into pBS. Each of these plasmids was used to generate a tri-cistronic helper cassette. Each envelope plasmid received the CD8-hygromycin cassette described above. The gag/pol plasmid received either of two cassettes. One consisted of an EMCV IRES linked to the gene encoding a cytoplasmic domain defective CD4 (another cell surface marker) linked to an EMCV IRES linked to the gene for histidinol resistance. The second cassette consisted of an EMCV IRES linked to the gene encoding green fluorescent protein linked to and FDV IRES linked to the gene encoding puromycin resistance.

Since all of these tricistronic cassettes are used similarly to introduce packaging functions into cells, introduction of the single gene helper cassette will be described. Introduction of the separated helper functions simply requires additional quantitative and qualitative selection steps.

13.3 EXPRESSION VEHICLES.

The helper cassettes described above must be functionally linked to sequences that promote expression in mammalian cells. These constructs can then be introduced into cell lines to create a functional packaging system. In general two options are available. The single helper cassette can be cloned in functional association with a strong promoter (e.g. CMV) in a plasmid that can replicate in the presence of SV40 T antigen. This allows amplification of the plasmid episomally. In some cases this is followed by high copy integration into the genome. Such a plasmid can also be used in the absence of SV40 T-antigen to achieve somewhat lower copy numbers. For this purpose the single helper cassette has be inserted into pcDNA3 (Invitrogen). Alternatively, the helper cassette can be placed in association with a strong promoter on a vector that replicates as a stable episome. Two such systems are in common use. The first is based upon Epstein Barr Virus. EBV-based vectors replicate via oriP which requires EBNA for function. A particularly useful vector has been produced by Invitrogen (pCEP-4). This vector has been modified to remove the hygromycin resistance cassette and the helper cassette has been inserted downstream of the CMV promoter. Upon transfection into our chosen host cell line, this vector can achieve stable copy numbers of >20/cell. The final choice is a set of vectors based upon bovine papilloma virus. Unfortunately, these vectors will not replicate in our host cell of choice and we must therefore obtain modified BPV vectors in which viral functions are expressed from a constitutive promoter that functions in our chosen cell type. These modified BPV vectors can achieve copy numbers that range from 100–1000/cell.

13.4 CELL FOR THE GENERATION OF PACKAGING CELL LINES

Human 293 cells have been chosen for the generation of packaging cell lines. These cells can support replication from SV40-based systems and EBV based systems. These can also be used for the high copy number, modified BPV systems. In particular, a subline of human 293 cells (293T) shows extremely high transfection efficiencies (this is critical for the production of high-complexity libraries) and contains a temperature sensitive SV40 large T antigen that can support conditional replication of SV40-based vectors.

13.5 SELECTION OF PACKAGING CELL CLONES

Human 293T cells will be transfected with either the single helper plasmid or the two separate helper plasmids in the vectors described above. Transfected cells will be placed in selective media containing standard concentrations of hygromycin (75 µg/ml) or hygromycin plus puromycin (1.5 µg/ml). Following successful selection of stably transfected clones, high-expressing cells will be selected by FACS analysis following staining with antibodies directed against the cell surface markers or by direct detection of gfp. The 5% of clones which display the highest expression levels will be recovered and plated again in selective media. Cells will be passed into a media containing a 50% higher concentration of each drug and the 5% of surviving cells which display the highest marker expression will be passed through another round of this procedure. At each round, levels of elaborated reverse transcriptase and transfection rates are assessed. After several rounds, at a time at which subsequent rounds fail to increase reverse transcriptase expression or at which high drug concentrations result in a reduced transfection rate, single cell clones will be chosen and analyzed for the ability to produce high titer virus. The ability to enforce direct selection for the viral helper cassettes should allow not only selection of the most efficient packaging cells but should also allow for continuous selection for maintenance of high efficiency packaging function.

14. EXAMPLE

TARGET ANTISENSE EXPRESSION-DERIVATION OF A FUNCTIONAL KNOCKOUT

Single gene antisense libraries in the MaRXIIg vectors can be used to created targeted functional knockouts of individual genes. This can be accomplished irrespective of prior knowledge of the phenotype of the knockout by creating an indirect selection for loss of gene function. This is accomplished by creating a quantifiable marker that serves to report the levels of expression of a particular gene. This can be created in any of a number of ways as described in the text of the application. The most straightforward is to create a fusion protein and this will be the example given.

The coding sequence of the protein of interest is fused to a reporter, in this case, the green fluorescent protein. This fusion should be prepared so that the 5' and 3' untranslated sequences are present in the construct. The entire cassette, including untranslated sequences is placed within a retroviral vector that promotes constitutive expression. Inducible vectors can also be used if expression of the fusion protein is deleterious. This vector is inserted into cells of a species distinct from the species from which the knock-out target is derived. For example, mink cells would make a reasonable screening host for human proteins. A population of cells showing uniform fluorescence is selected by single-cell cloning or by FACS. A single-gene, unidirectional antisense library is constructed from the transcript encoding the target gene (see above0 in one of the MaRXIIg vectors. This library is used to infect cells that express the fluorescent fusion. By FACS sorting, cells which no longer express the fusion are identified. These are cloned as single cells. A subset of these will express antisense transcripts which effectively inhibit expression of the fluorescent fusion protein, and a subset will simply have lost fusion protein expression independent of an introduced antisense (revertants). Effective antisense can be distinguished from revertants by the ability of Cre recombinase to rescue fluorescent protein expression. Cell clones in which fluorescence is rescued by Cre will serve as a source for the recovery of viruses carrying antisense fragments which can be used to create functional knockouts in any desired cell line. It should be noted that this procedure is quantitative and qualitative; by FACS sorting, the most effective fragments can be identified as those able to quantitatively reduce fluorescence to the greatest extent. Furthermore, by replacing the CMV promoter in the MarxIIg and MaRXIIg-dccmv with an inducible promoter (in combination with a self-inactivating LTR), conditional knockouts can be created.

15. EXAMPLE

ACTIVATION OF THE TELOMERASE ENZYME

Telomerase is an almost universal marker for tumorigenesis. Activity is, however, absent in normal cells. Activity can be induced in a subset of normal cells (e.g., epithelial cells and keratinocytes) by introduction of the E6 protein from HPV-16. This induction is independent of the ability of E6 to direct degradation of p53. In order to investigate the processed that lead to the induction of telomerase in tumors, we have devised an in vitro screen for genes that can induce telomerase activity in normal human mammary epithelial cells (HMEC).

Pools of cDNAs comprising from 100–100 clones each (either in the sense orientation or in the antisense orientation in the MaRXIIg vector series) are introduced into HMEC cells. These are selected for expression of cDNA and then used to prepare lysates for the assay of telomerase activity. Cell lysates are tested using a highly sensitive telomerase assay which is capable of detecting two telomerase-positive cells among 20,000 telomerase-negative cells. Those pools which upon infection cause the induction of telomerase activity in HMEC cells are subdivided into smaller pools. Sub-pools are again used for the infection of HMEC cells which are subsequently assayed for telomerase activity. Successive rounds of this procedure can identify an individual clone that acts as an inducer of the telomerase enzyme.

Such a clone could represent a direct regulator of the enzyme itself or of the expression of a component of the enzyme. Alternatively, such a clone could act as a regulator of cell mortality. Changes induced by the expression of such a clone could induce the telomerase enzyme as only one aspect of a more global change in cellular behavior.

DEPOSIT OF MICROORGANISMS

*E. coli* strain XL-1 carrying plasmid pMaRXII, was deposited on Sep. 20, 1996 with the Agricultural Research Service Culture Collection (NHRL), under the provisions of the Budapest Treaty on the International Recognition of the Deposit of Microorganisms for the Purposes of Patent Procedures and assigned accession number .

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A retroviral vector comprising:
   (a) a 3' LTR sequence for integration of the vector into chromosomal DNA of a host cell;
   (b) a heterologous nucleic acid sequence to be transcribed in the host cell, or one or more restriction cloning sites for cloning the heterologous nucleic acid sequence into the vector;
   (c) proviral excision elements, contained within the 3' LTR sequence, for excising a proviral form of the vector from chromosomal DNA.

2. The vector of claim 1, wherein said heterologous nucleic acid sequence comprises a cDNA or gDNA coding sequence for a polypeptide.

3. A retroviral library comprising a multiplicity of the retroviral vectors of claim 1, having different heterologous sequences.

4. A retroviral particle including the retroviral vector of claim 1.

5. An integrated provirus derived from the retrovirus of claim 1, said provirus integrated into cells isolated in culture.

6. An excised provirus obtained by the excision of a provirus integrated by the vector of claim 1.

7. The vector of claim 1 wherein said vector is a replication-deficient virus.

8. The vector of claim 1, wherein said vector further includes a proviral recovery element for isolating the vector from a mixture of nucleic acids.

9. The vector of claim 1, wherein said excision elements comprise enzyme-assisted site-specific integration sequences.

10. The vector of claim 9, wherein said excision elements include recombinase target sites.

11. The vector of claim 10, wherein said recombinase target sites are target sites for Cre recombinase or Flp recombinase.

12. The vector of claim 1, wherein said excision elements include restriction enzyme sites.

13. The vector of claim 1, wherein said excision elements are positioned in the vector such that, upon excision of the vector from chromosomal DNA, the excised vector can be used directly to generate virus for subsequent rounds of infection.

14. The vector of claim 1, wherein said vector further includes a packaging signal for packaging the vector in an infectious viral particle.

15. The vector of claim 1, further comprising a polycistronic message cassette for transcribing the heterologous nucleic acid sequence as a polycistronic message.

16. The vector of claim 15, wherein said polycistronic message cassette comprises the heterologous nucleic acid sequence, or the restriction cloning sites for cloning the heterologous nucleic acid sequence, disposed in said vector proximal to one or more marker genes such that the heterologous nucleic acid sequence and marker gene(s) are transcribed as a polycistronic message.

17. The vector of claim 15, wherein said polycistronic message includes internal ribosome entry sites (IRES) between coding sequences of the message.

18. The vector of claim 8, wherein said proviral recovery element comprises a nucleic acid sequence specifically bound by a DNA binding polypeptide.

19. The vector of claim 1, 25 or 28, further comprising at least one bacterial origin of replication disposed in the vector such that, upon excision, the origin of replication is present in the provirus.

20. The vector of claim 19, wherein said bacterial origin of replication is a non-pUC ori.

21. The vector of claim 19, wherein said bacterial origin of replication is a single-stranded origin of replication.

22. The vector of claim 20, wherein said bacterial origin of replication is selected from the group consisting of RK2 OriV and f1 phage Ori.

23. The vector of claim 1, further comprising a selectable bacterial marker gene.

24. The vector of claim 23, wherein said selectable bacterial marker gene renders a bacterial host cell resistant to a drug or complements a cellular phenotype.

25. The vector of claim 23, wherein said selectable bacterial marker gene renders a bacterial host cell resistant to a drug selected from the group consisting of kanamycin/G418, zeocin, actinomycin, ampicillin, gentamycin, tetracycline, chloramphenicol and penicillin.

26. The vector of claim 1, further comprising a mammalian marker gene, the expression of which provides a detectable phenotype in a host cell.

27. The vector of claim 26, wherein expression of said mammalian marker gene renders the host cell resistant to a drug or complements a cellular phenotype.

28. The vector of claim 26, wherein said mammalian marker gene encodes a protein providing resistance to kanamycin/G418, hygromycin, mycophenolic acid or neomycin.

29. The vector of claim 26, wherein said mammalian marker gene encodes a fluorescent protein, or an enzyme which can alter the fluorescence of the host cell.

30. The vector of claim 29, wherein said mammalian marker gene encodes a green fluorescent protein.

31. The vector of claim 1, further comprising a lethal stuffer fragment, the expression of which provides a detectable phenotype in the host cell, the expression of the lethal stuffer fragment being dependent on the presence or absence in the vector of the heterologous nucleic acid sequence.

32. The vector of claim 1, 10 or 18, wherein said heterologous nucleic acid sequence includes a coding sequence for a polypeptide.

33. The vector of claim 32, wherein said coding sequence encodes an intracellular polypeptide.

34. The vector of claim 32, wherein said coding sequence encodes a secreted or cell surface polypeptide.

35. The vector of claim 1, wherein said heterologous nucleic acid sequence includes a genetic suppressor element.

36. The vector of claim 35, wherein said genetic suppressor element is selected from the group consisting of an antisense construct, a coding sequence for a dominant negative mutant or fragment of protein, and a ribozyme.

37. The vector of claim 1, further comprising a constitutive transcriptional regulatory sequence for regulating transcription of the heterologous nucleic acid in the host cell.

38. The vector of claim 1, further comprising an inducible transcriptional regulatory sequence for regulating transcription of the heterologous nucleic acid in the host cell.

39. The vector of claim 1, wherein said vector is incorporated in an artificial chromosome.

40. The vector of claim 1, wherein said retroviral vector is derived from a replication-deficient retrovirus lacking all or a portion of the retroviral gag, pol and/or env genes.

41. The vector of claim 1, wherein said retroviral vector is derived from pBABE.

42. The vector of claim 1, wherein said LTR sequences include said excision elements, and said excised vector can be used directly to generate packaged retroviral vectors.

43. The vector of claim 42, wherein said vector includes a self-inactivating LTR.

44. The vector of claim 1, wherein said vector is a closed circular nucleic acid.

45. The vector of claim 1, wherein said vector is a linear nucleic acid.

46. The vector of claim 1, wherein said vector is DNA.

47. The vector of claim 1, wherein said vector is DNA.

48. The vector of claim 1, wherein said vector is packaged in a viral particle.

49. A library of vectors comprising a population of vectors according to claim 1, 11 or 13, the library including vectors having different heterologous nucleic acid sequences.

50. The vector library of claim 49, wherein said library comprises, as the heterologous nucleic acid sequences, a population of cDNA sequences.

51. The vector library of claim 50, wherein said cDNA library is a normalized cDNA library.

52. The vector library of claim 49, wherein said library comprises, as the heterologous nucleic acid sequences, a population of coding sequences for a peptide library.

53. The vector library of claim 52, wherein said peptide library is a constrained peptide library, as for example, part of a fusion protein.

54. The vector library of claim 49, wherein said library comprises, as the heterologous nucleic acid sequences, a population of genetic suppressor elements.

55. The vector library of claim 54, wherein said genetic suppressor elements are selected from the group consisting of an antisense constructs, coding sequences for fragments of proteins and ribozymes.

56. The vector of claim 8, wherein said provirus recovery element is a lac operator nucleic acid sequence, a tet operator nucleic acid sequence or a lambda operator nucleic acid sequence.

57. The vector of claim 18, wherein said DNA binding polypeptide is a lac repressor, a tet repressor or a lambda repressor.

58. The retroviral vector library of claim 3, wherein said cDNA library is a normalized cDNA library.

59. The retroviral library of claim 3, wherein said library is a single-stranded library.

60. The excised provirus of claim 6, wherein said excised provirus is circularized.

* * * * *